(12) United States Patent
Cheng et al.

(10) Patent No.: US 9,295,651 B2
(45) Date of Patent: Mar. 29, 2016

(54) NANOCONJUGATES AND NANOCONJUGATE FORMULATIONS

(75) Inventors: Jianjun Cheng, Champaign, IL (US); Rong Tong, Cambridge, MA (US)

(73) Assignee: The Board of Trustees of the University of Illinois, Urbana, IL (US)

(*) Notice: Subject to any disclaimer, the term of this patent is extended or adjusted under 35 U.S.C. 154(b) by 445 days.

(21) Appl. No.: 13/518,836

(22) PCT Filed: Dec. 23, 2010

(86) PCT No.: PCT/US2010/062030
§ 371 (c)(1),
(2), (4) Date: Jan. 4, 2013

(87) PCT Pub. No.: WO2011/079279
PCT Pub. Date: Jun. 30, 2011

(65) Prior Publication Data
US 2013/0101672 A1    Apr. 25, 2013

Related U.S. Application Data

(60) Provisional application No. 61/289,893, filed on Dec. 23, 2009.

(51) Int. Cl.
| | | |
|---|---|---|
| A61K 9/14 | (2006.01) | |
| A61K 38/38 | (2006.01) | |
| A61K 47/30 | (2006.01) | |
| A61K 47/42 | (2006.01) | |
| A61K 47/48 | (2006.01) | |
| A61K 9/16 | (2006.01) | |
| A61K 9/00 | (2006.01) | |
| A61K 9/51 | (2006.01) | |

(52) U.S. Cl.
CPC ............ A61K 9/1658 (2013.01); A61K 9/0019 (2013.01); A61K 9/5169 (2013.01); A61K 47/482 (2013.01); A61K 47/48215 (2013.01); A61K 47/48907 (2013.01)

(58) Field of Classification Search
None
See application file for complete search history.

(56) References Cited

U.S. PATENT DOCUMENTS

| | | | |
|---|---|---|---|
| 6,346,274 B1 | 2/2002 | Koll et al. | |
| 6,346,627 B1 | 2/2002 | Liotta et al. | |
| 7,018,609 B2 | 3/2006 | Hwang Pun et al. | |
| 7,399,486 B2 | 7/2008 | Lee et al. | |
| 2005/0058603 A1* | 3/2005 | Gao et al. | 424/9.32 |
| 2007/0093547 A1* | 4/2007 | Desai et al. | 514/449 |
| 2008/0248126 A1* | 10/2008 | Cheng et al. | 424/497 |

OTHER PUBLICATIONS

Hans, M.L. et al., "Biodegradable nanoparticles for drug delivery and targeting," Current Opinion in Solid State and Materials Science 6 (2002) 319-327.*
F.B. Landry et al., "Degradation of poly(D,L-lactic acid) nanoparticles coated with albumin in model digestive fluids (USP XXII)," Biomaterials 17 (1995) 715-723.*
Chang et al., "Stabilization of tetanus toxoid in poly (DL-lactic-co-glycolic acid) microspheres for the controlled release of antigen," Pharmaceutical Sciences (1996) 85 (2): 129-132.
Lee et al., "Hyaluronic acid—paclitaxel conjugate micelles: Synthesis, characterization, and antitumor activity," Bioconjugate Chem. (2008) 19: 1319-1325.
Stolnik et al., "Surfact modification of poly(lactide-co-glycolide) nanospheres by biodegradeable poly(lactide)-poly (ethylene glycol) copolymers," Pharmaceutical Research (1994) 11 (12): 1800-1808.
Zhang et al., "Synthesis and characterization of the paclitaxel/MPEG-PLA block copolymer conjugate," Biomaterials (2005) 26: 2121-2128.
International Search Report (Form PCT/ISA/210) for corresponding International Application No. PCT/US2010/062030 mailed Sep. 29, 2011.
Written Opinion (Form PCT/ISA/237) for corresponding International Application No. PCT/US2010/062030 mailed Sep. 29, 2011.
Chinese Office Action for corresponding application No. CN2010800625510 dated Aug. 14, 2013.
Office Action Search Report for corresponding application No. CN2010800625510 dated Jul. 25, 2013.
Tong et al., "Paclitaxel-Initiated, Controlled Polymerization of Lactide for the Formulation of Polymeric Nanoparticulate Delivery Vehicles," Angew. Chem. Int. Ed. (2008) 47: 4830-4834.
Allard, Emilie et al., "Convection-Enhanced Delivery of Nanocarriers for the Treatment of Brain Tumors," biomaterials 30 (2009) 2302-2318.
Verrecchia, T. et al., "Non-Stealth (Poly(Lactic Acid/Albumin)) and Stealth (Poly(Lactic Acid-Polyethylene Glycol)) Nanoparticles as Injectable Drug Carriers," Journal of Controlled Release 36 (1995) 49-61.
Corresponding European Extended Search Report dated Sep. 3, 2015.

* cited by examiner

*Primary Examiner* — Tracy Vivlemore
*Assistant Examiner* — Monica Shin
(74) *Attorney, Agent, or Firm* — Haukaas Fortius PLLC; Michael H. Haukaas

(57) ABSTRACT

The invention provides a drug-polymer nanoconjugate that includes a drug covalently bonded to a polymer. The nanoconjugate can include a block copolymer coating and/or an albumin coating. The drug of the drug-polymer nanoconjugate can be one or more of a variety of therapeutic agents linked to the polymer through ether or thioether linkages formed from hydroxyl or thiol groups of the drug. The albumin coating can substantially or completely retard or prevent aggregation of the nanoconjugates in solid form or in solution. The invention further provides compositions that include a plurality of drug-polymer nanoconjugates, as well as methods for using the drug-polymer nanoconjugates, such as in therapeutic or diagnostic applications.

18 Claims, 13 Drawing Sheets

| [LA]/[Ptxl] | $M_{cal}$ (x10³g/mol) | $M_n$ (x10³g/mol) | MWD |
|---|---|---|---|
| 50 | 8.1 | 7.8 | 1.04 |
| 100 | 15.3 | 12.7 | 1.03 |
| 200 | 29.7 | 28.1 | 1.02 |

NANOCONJUGATES AND NANOCONJUGATE FORMULATIONS

RELATED APPLICATIONS

This application is a National Stage Application of PCT/US2010/062030, filed Dec. 23, 2010, which claims priority under 35 U.S.C. §119(e) to U.S. Provisional Patent Application No. 61/289,893, filed Dec. 23, 2009, and which applications are incorporated herein by reference. A claim of priority to all, to the extent appropriate is made.

GOVERNMENT SUPPORT

This invention was made with government support under Grant No. DMR-0748834-CAREER, awarded by the National Science Foundation. The United States Government has certain rights in the invention.

BACKGROUND OF THE INVENTION

Polymeric nanoparticles (NPs) are attractive drug delivery vehicles. Various forms of the NPs have been studied for the delivery of chemotherapeutic agents to treat cancer. In these polymeric NPs, chemotherapeutic agents are either encapsulated in polymer matrices or covalently conjugated to polymers via hydrolysable or enzymatically degradable linkages. Systemically administered NPs are ideally able to bypass the recognition of the reticuloendothelial system (RES), extravasate at the leaky tumor vasculatures, penetrate and homogeneously distribute in solid tumor tissues, get internalized by the target cancer cells, penetrate cellular and subcellular membranes, and then release their drug cargo in the cytoplasma of the target cancer cells in a sustained manner. NPs that can successfully overcome all these systemic, tissue, and cellular barriers are urgently needed. In addition to these translational barriers, NPs must be able to be stored for periods of time before clinical use. Many NPs aggregate in solution or in a lyophilized state. Aggregation can destroy the utility of these compositions by making them unable to accomplish one or more of the previously mentioned objectives. Accordingly, there is a need for NPs that can be prepared, stored, and systemically administered without aggregation.

SUMMARY

Nanoconjugates (NCs) have been developed that circumvent many of the translational barriers to providing clinically useful drug formulations. The invention described herein provides a drug-polymer nanoconjugate that includes a drug covalently bonded to a polymer. The nanoconjugate can include a block copolymer coating and/or an albumin coating. The drug-polymer nanoconjugate includes one or more drugs and one or more polymers, where one or more drugs of the drug-polymer nanoconjugate is located at an initiation point of a polymer of the drug-polymer conjugate, one or more of the drugs include at least one hydroxyl or thiol moiety prior to initiation of polymerization, and such drug is covalently bonded to the polymer at the location of a hydroxyl or thiol moiety of the drug, thereby forming an ether or thioether linkage between the drug and the polymer.

The polymer of the drug-polymer nanoconjugate can include monomers derived from cyclic esters, cyclic carbonates, cyclic phosphates, cyclic siloxanes, cyclic phosphazanes, or cyclic peptides or amino acids. Accordingly, one or more of the polymers of the drug-polymer nanoconjugate can include polyesters, polycarbonates, polyphosphates, polysiloxanes, polyphosphazanes, polypeptides, or oligomers of amino acids. The block copolymer coating can include PEG and/or lactide blocks, and the block copolymer coating can be coated with albumin. The amount of albumin used to coat the nanoconjugate can be an amount effective to at least substantially prevent aggregation of the drug-polymer nanoconjugate to other drug-polymer nanoconjugates. In a variety of embodiments, the albumin completely prevents aggregation of the drug-polymer nanoconjugate to other drug-polymer nanoconjugates, either in a solid state, or in an aqueous medium. The nanoconjugate can include one or more cell-targeting agents covalently bonded to the surface of the drug-polymer nanoconjugate or to the block copolymer coating. The cell-targeting agents can selectively target, for example, cancer cells.

The invention also provides a composition that includes a plurality of nanoconjugates described herein wherein the composition of nanoconjugates has a monomodal nanoconjugate particle size distribution. The composition can be a dry powder composition, or a composition formulated for intravenous injection that includes, for example, a pharmaceutically acceptable diluent or carrier.

The invention further provides a method for delivering the drug of a drug-polymer nanoconjugate to the surface or interior of a cell. The method can include contacting a cell with a drug-polymer nanoconjugate described herein, so that the drug-polymer conjugate associates with the cell for a period of time sufficient for the drug-polymer nanoconjugate to release the drug from the polymer, thereby delivering the drug to the surface or interior of the cell.

In other embodiments, the drug of the drug-polymer conjugate can be exchanged for a variety of useful chemical species, such as chemical reagents, diagnostics, contrast agents, reporter molecules, dyes, and the like, for the preparation of particulate delivery systems.

The invention further provides for the use of drug-polymer nanoconjugates for the manufacture of medicaments useful for the treatment of diseases in a mammal, such as a human. Compositions of drug-polymer nanoconjugates can be used, for example, in medical therapy or diagnostic evaluation. The medical therapy can be treating cancer, for example, prostate cancer, breast cancer, lung cancer, pancreatic cancer, or colon cancer.

In another embodiment, the invention provides an aggregation resistant nanoparticle composition comprising a plurality of polymer-based nanoparticles. Such nanoparticles include a coating of albumin, wherein the amount of albumin is effective to reduce or prevent aggregation of the nanoparticles.

The average diameter of the polymer-based nanoparticles can be less than about 200 nm, less than 100 nm, or less than 50 nm, without the coating of albumin. After the particles have been coated with albumin, the average particle diameter is typically less than about 250 nm, less than about 200 nm, or less than about 175, for example, about 50 nm to about 150 nm. The polymer-based nanoparticles can be nanoparticles that self-stabilize when in contact with an aqueous solution in the absence of the coating of albumin. The ratio of the mass of albumin coating to the total mass of nanoparticles can be about 2:1 to about 20:1, typically about 3:1 to about 10:1. The nanoparticles coated with albumin can remain non-aggregated for an extended period of time under ambient conditions, for example, in the presence of air with 50% humidity for more than about 12 hours, at room temperature (~23° C.).

In yet another embodiment, the invention provides a method of reducing or eliminating nanoparticle aggregation that includes contacting a sample of nanoparticles in solvent system and an aqueous solution comprising albumin, wherein the amount of albumin in the aqueous solution is at least 2.5 times the total mass of the nanoparticles. The albumin coated nanoparticles can then be lyophilized, to provide dry non-aggregated nanoparticles.

An additional embodiment provides a composition that includes non-aggregated PLA-PEG-PLA block polymer coated drug-polymer nanoconjugate particles in phosphate buffered saline. The average diameter of the coated particles can be about 20 nm to about 200 nm, wherein the particle size distribution of the coated particles is monomodal.

In one embodiment, the invention provides a method of preparing nanoparticles in phosphate buffered saline including dissolving a drug-polymer nanoconjugate and a PLA-PEG-PLA block polymer in an organic solvent, wherein the mass ratio of the drug-polymer nanoconjugate to the block copolymer coating is about 0.75 to about 1.25. The drug-polymer nanoconjugate and the PLA-PEG-PLA block polymer can be precipitated in a buffer, for example, at least about 20 volumes of phosphate buffered saline, to provide drug-polymer nanoconjugate particles coated with the PLA-PEG-PLA block polymer, wherein the coated particles remain non-aggregated in the phosphate buffered saline for more than 30 minutes.

In a further embodiment, the invention provides a method of reducing or eliminating nanoparticle aggregation, including contacting a plurality of nanoparticles with a block copolymer that comprises poly(ethylene glycol) and poly(lactide) blocks to provide block copolymer coated particles. The block copolymer coated particles can also be coated with albumin, thereby reducing or eliminating nanoparticle aggregation of the nanoparticles. The block copolymer can be a PLA-PEG-PLA block copolymer, and the nanoparticles can be a drug-polymer nanoconjugate composition described herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example or a certain aspect of the invention, however, one skilled in the art will understand that portions of the example or aspect may be used in combination with other examples or aspects of the invention. According to various embodiments:

FIG. 8 The stability of NCs in PBS solution. ■: A mixture of Ptxl-LA$_{100}$ and LE5 in DMF (w/w=1/1, Ptxl-LA$_{100}$=4 mg/mL) was co-precipitated in 1× PBS (DMF/PBS=1/40 (v/v)). ●: A mixture of Ptxl-LA$_{100}$ and LE5L in DMF (w/w=1/1, Ptxl-LA$_{100}$=4 mg/mL) was co-precipitated in 1×PBS (DMF/PBS=1/40 (v/v)). ▲: A mixture of Ptxl-LA$_{100}$ and LE5L in acetone (w/w=1/1, Ptxl-LA$_{100}$=2 mg/mL, 100 µL) was co-precipitated in water (4 mL). The obtained NC had a diameter of 88.9 nm with a polydispersity of 0.092. The resulting NC solution was mixed with an aqueous solution of BSA (500 µL, 12 mg/mL) and the mixture was lyophilized for 16 hours at −50° C. The resulting powder was reconstituted with 2 mL of water followed by the addition of a concentrated PBS solution (222 µL, 10×). The mixture was stirred for 5 minutes at room temperature and analyzed by DLS.

FIG. 9. Linear correlation of Ptxl-LA$_{100}$/LE5L NC size with Ptxl-LA$_{100}$ concentration in DMF when the mixture of Ptxl-LA$_{100}$/LE5L was co-precipitated in water or in PBS.

DETAILED DESCRIPTION

Definitions

Figure 1:
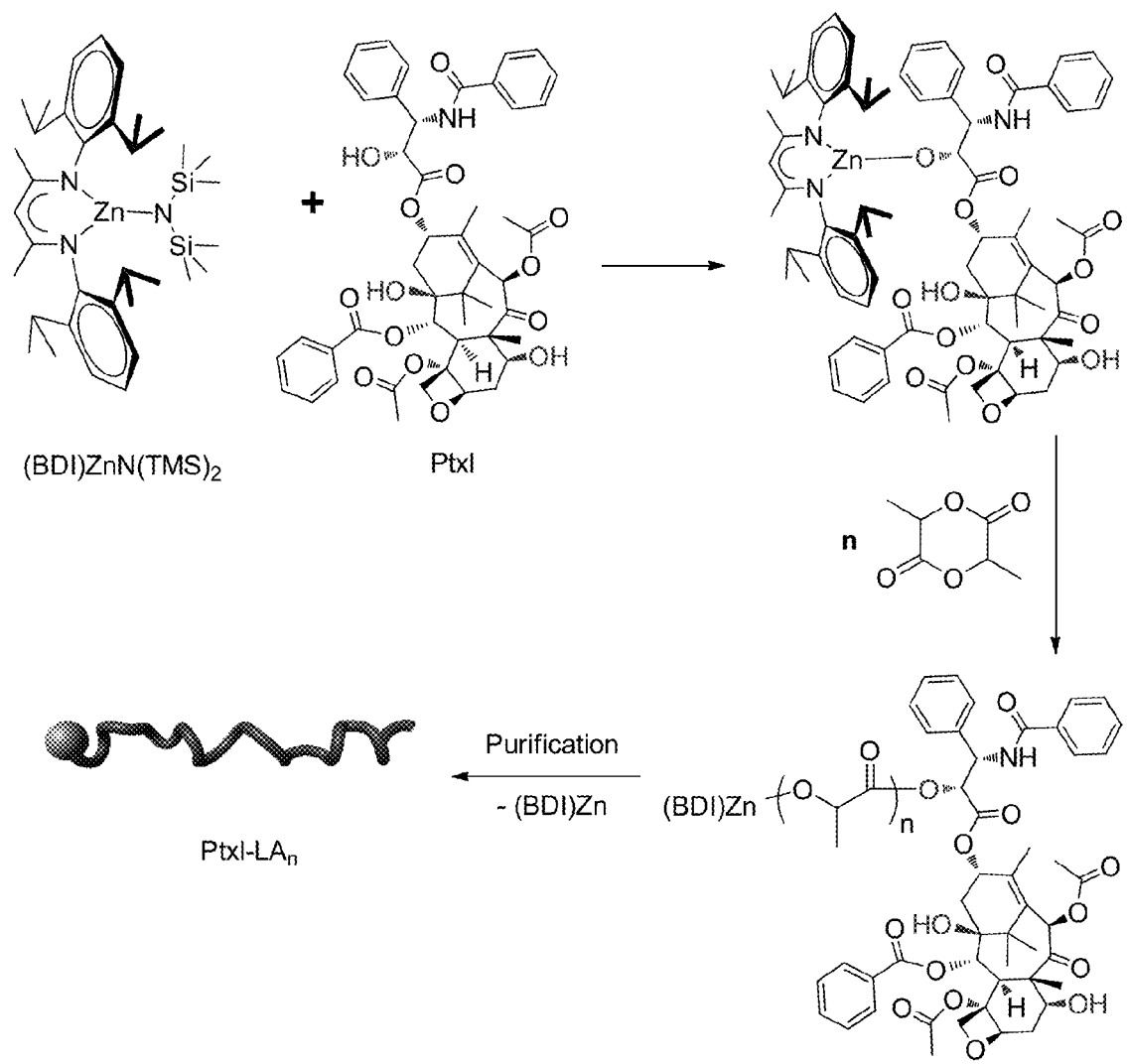
FIG. 1. (a) Regioselective initiation and controlled lactide (LA) polymerization mediated by a Ptxl/(BDI)ZnN(TMS)$_2$ complex to provide a Ptxl-PLA conjugate. (b) Formulation of Ptxl-PLA NCs through i) nanoprecipitation of Ptxl-PLA; ii) nanoprecipitation of Ptxl-PLA followed by coating with PLA-PEG; iii) co-precipitation of Ptxl-PLA and PLA-PEG; and iv) co-precipitation of Ptxl-PLA and PLA-PEG-PLA. NPP=nanoprecipitation; CPP=co-precipitation.
Figure 1:
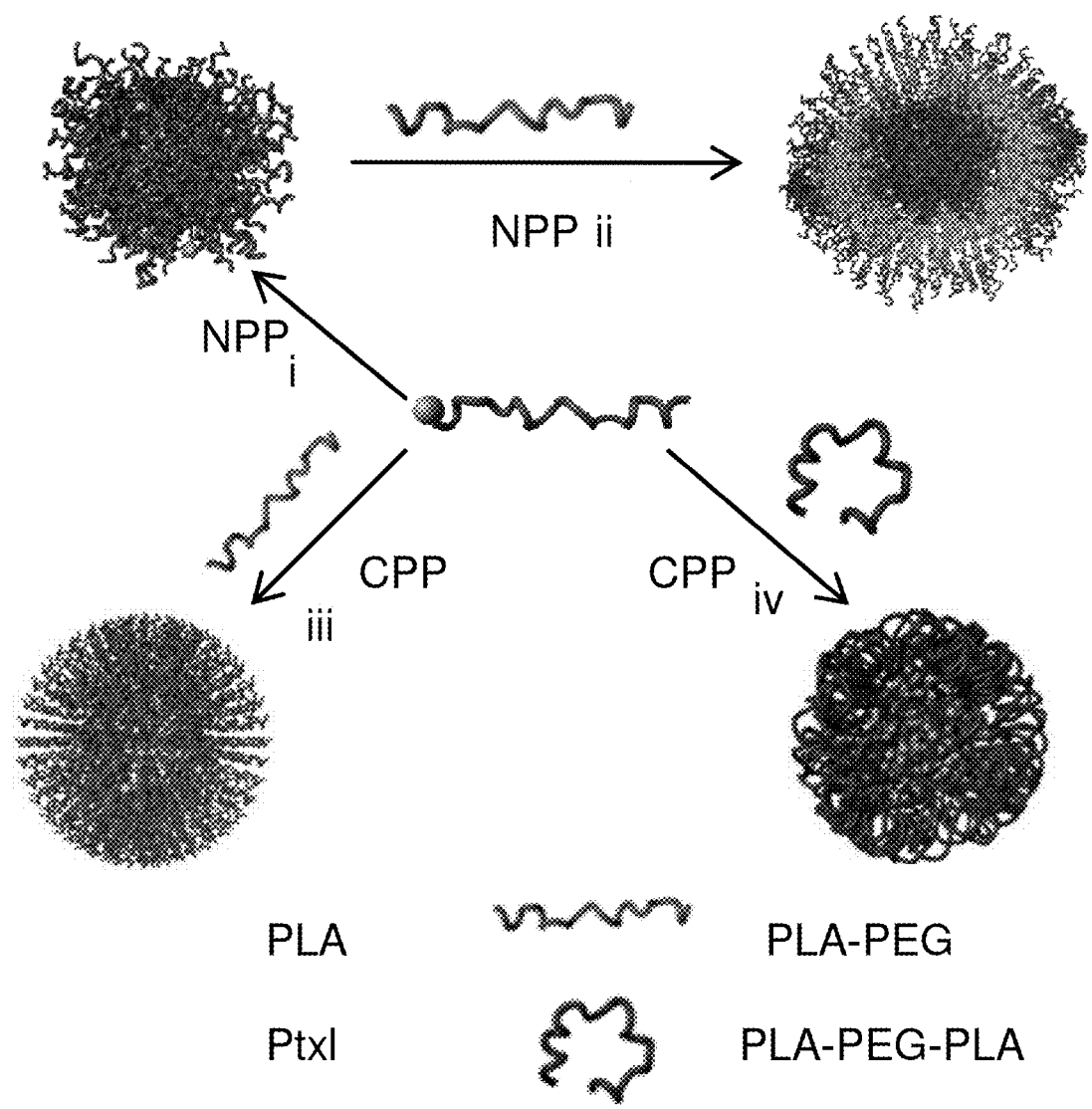

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic in connection with other embodiments, whether or not explicitly described.

The term "comprising" is synonymous with "including," "containing," or "characterized by," and is inclusive or open-ended and does not exclude additional, unrecited elements or method steps. The term "consisting of" excludes any element, step, or ingredient not specified in the claim element. The term "consisting essentially of" does not exclude materials or steps that do not materially affect the basic and novel characteristics of the claim. In each instance herein, any of the terms "comprising", "consisting essentially of" or "consisting of" may be replaced with either of the other two terms. The invention illustratively described herein suitably may be practiced in the absence of any element or elements, limitation or limitations which is not specifically disclosed herein.

The term "and/or" means any one of the items, any combination of the items, or all of the items with which this term is associated. The phrase "one or more" is readily understood by one of skill in the art, particularly when read in context of its usage.

The singular forms "a," "an," and "the" include plural reference unless the context clearly dictates otherwise. Thus, for example, a reference to "a nanoconjugate" includes a plurality of such nanoconjugate. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

The term "about" can refer to a variation of ±5%, ±10%, ±20%, or ±25% of the value specified. For example, "about 50" percent can in some embodiments carry a variation from 45% to 55%. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges disclosed herein also encompass any and all possible subranges and combinations of subranges thereof as well as the individual values making up the range, particularly integer values. A recited range (e.g., weight percents) includes each specific value, integer, decimal, or identity within the range. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio. Accordingly, specific values listed herein for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention also envisages the explicit exclusion of any one or more of members of a recited group.

The term "alkyl" refers to a monoradical of a branched or unbranched (straight-chain or linear) saturated hydrocarbon or to cycloalkyl groups having one or more rings. Unless otherwise indicated, typical alkyl groups have 1 to 20 carbon atoms, for example, about 1-10 carbon atoms. Short alkyl groups are those having 1 to 6 carbon atoms, including methyl, ethyl, propyl, butyl, pentyl and hexyl groups, including all isomers thereof. Long alkyl groups are those having about 8 to about 20 carbon atoms, for example, about 12 to about 20 carbon atoms, as well as those having 12-20 and those having 16-18 carbon atoms. The term "cycloalkyl" refers to cyclic alkyl groups having 3 to 20 carbon atoms having a single cyclic ring or multiple condensed rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated, alkyl groups including cycloalkyl groups are optionally substituted as defined below.

The term "alkenyl" refers to a monoradical of a branched or unbranched unsaturated hydrocarbon group having one or more double bonds or to a cycloalkenyl group having one or more rings wherein at least one ring contains a double bond. Unless otherwise indicated, alkyl groups have 1 to 20 carbon atoms, for example, 1 to about 10 carbon atoms. Alkenyl groups may contain one or more double bonds (C═C), which may be conjugated or unconjugated. Alkenyl groups can include those having 1 or 2 double bonds, including omega-alkenyl groups. Short alkenyl groups can be those having 2 to 6 carbon atoms including ethylene (vinyl), propylene, butylene, pentylene and hexylene groups, including all isomers thereof. Long alkenyl groups include those having 8-20 carbon atoms, for example, those having 12-20 carbon atoms, as well as those having 12-20 carbon atoms or those having 16-18 carbon atoms. The term "cycloalkenyl" refers to cyclic alkenyl groups of from 3 to 20 carbon atoms having a single cyclic ring or multiple condensed rings in which at least one ring contains a double bond (C═C). Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl, as well as multiple ring structures. Unless otherwise indicated, alkyl groups including cycloalkyl groups are optionally substituted as defined below.

The term "alkynyl" refers to a monoradical of an unsaturated hydrocarbon having one or more triple bonds (C≡C). Unless otherwise indicated, alkyl groups have 1 to 20 carbon atoms, for example, those that contain 1-10 carbon atoms. Alkynyl groups include ethynyl, propargyl, and the like. Short alkynyl groups are those having 2 to 6 carbon atoms, including all isomers thereof. Long alkynyl groups are those having 8-20 carbon atoms, such as those having 12-20 carbon atoms, as well as those having 12-16 carbon atoms or those having 16-18 carbon atoms. The term "cycloalkynyl" refers to cyclic alkynyl groups of from 3 to 20 carbon atoms having a single cyclic ring or multiple condensed rings in which at least one ring contains a triple bond (C≡C). Unless otherwise indicated, alkyl groups including cycloalkyl groups are optionally substituted as defined below.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 20 carbon atoms and those containing 6-12 carbon atoms. Unless otherwise noted, aryl groups are optionally substituted as described herein. The term aryl includes "arylalkyl" groups, which refers to a group that contains at least one alkyl group and at least one aryl group, the aryl group may be substituted on the alkyl group (e.g., benzyl, —CH$_2$—C$_6$H$_5$) or the alkyl group may be substituted on the aryl group (e.,g., tolyl, —C$_6$—H$_4$—CH$_3$). Unless otherwise noted, either the alkyl or the aryl portion of the arylalkyl group can be substituted as described herein.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. When a compound or composition is described herein such that a particular isomer, enantiomer or diastereomer of the compound is not specified, for example, in a formula or in a chemical name, that description is intended to include each isomers and enantiomer of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quatemized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts for a given application. In specific applications, the selection of a given anion or cation for preparation of a salt may result in increased or decreased solubility of that salt.

The invention provides various conjugates of polymers or oligomers. The polymer is typically a chemical species containing a plurality of repeating units that are bonded to each other. A polymer may contain more than one different repeating unit. The repeating unit typically derives from polymerization of a monomer. A copolymer specifically refers to a polymer containing two or more structurally different repeating units. The different repeating units of a polymer may be randomly ordered in the polymer chain or the same repeating units may be grouped into contiguous blocks in the polymer. When there are contiguous blocks of the two or more repeating units in a polymer, the polymer is a block co-polymer. As used herein the term polymer refers to a chemical species containing more than about 10 repeating units. The term oligomer is used to refer to a chemicl species having two to about ten repeating units.

The term "particle" refers to a particle having any given shape that has a size that is useful for in vivo delivery by some administration method. The particles may be micelles, aggregates, spheres, or an irregular shape. The term "particle size" is used herein as it is generally used in the art and is determined by methods well know to those of skill in the art. A value recited for size is the average diameter of a particle, or the average width of an irregularly shaped particle.

The "polydispersity" of a polymer refers to the distribution of molecular weights of polymers in a given sample. The Polydispersity Index (PDI) is a specific measure of polydispersity and is the weight average molecular weight divided by the number average molecular weight. PDI relates to the distribution of individual molecular weights in a given sample of polymers. PDI can be determined using Gel Permeation Chromatography (GPC). As the polymer chains in a given sample approach uniform chain length, PDI approaches 1.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term drug includes "pharmaceutically acceptable salts" of drugs as well as prodrugs. The term "prodrug", as used herein, means a compound that is convertible in vivo by metabolic means (e.g., by hydrolysis) to a drug.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound or composition described herein, or an amount of a combination of elements described herein, e.g., an amount effective to treat or prevent a disease or disorder, or to treat the symptoms of the disease or disorder, in a host. Thus, an "effective amount" generally means an amount that provides the desired effect.

Accordingly, the term "therapeutically effective amount," refers to the amount a given drug that, when administered to the individual in the particulate form, is effective to at least partially treat the disorder, disease or condition from which the individual is suffering, or to at least partially ameliorate a symptom of such disorder, disease or condition. As is understood in the art, the therapeutically effective amount of a given compound will depend at least in part upon, the mode of administration, any carrier or vehicle (e.g., solution, emulsion, etc.) employed, the specific disorder or condition, and the specific individual to whom the compound is to be administered (age, weight, condition, sex, etc.). The dosage requirements needed to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined by techniques well understood in the art.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. For example, the compositions described herein can be used to inhibit the growth of a tumor or group of cells.

As used herein, the phrases "albumin coating" and "coating of albumin" refer to a set of conditions where albumin is associated with a nanoparticle to a degree sufficient to at least substantially prevent aggregation of the nanoparticle with other similar particles. In some embodiments, enough molecules of albumin may be in contact with a nanoparticle, for example, through electrostatic interactions, or the like, to form a protective barrier around the nanoparticle. In other embodiments, enough albumin may be present in the vicinity of a nanoparticle to provide lyoprotectant properties to the nanoparticle and neighboring nanoparticles, such as when nanoparticles are co-formulated with albumin, such as in an amount of that is effective to significantly reduce or prevent aggregation. Lyoprotectant properties refer to the property of albumin to substantially reduce or prevent aggregation of nanoparticles that are co-formulated with an effective amount of the albumin, such as when albumin is co-formulated with nanoparticles before lyophilizing the formulation.

The phrase effective "to at least substantially prevent aggregation" refers to the property of reducing aggregation to a degree such that the non-aggregated composition can be useful for its intended purpose. The phrase can include a complete lack of aggregation, for example, as determined by ocular inspection, or by a ratio of lyophilized particle size to pre-lyophilized particles of less than three.

The terms "monomodal" refers to a particle size distribution where a collection of particles (e.g., nanoconjugates, powders, granules, beads, crystals, etc.) have a single clearly discernable maxima on a particle size distribution curve (e.g., where weight percent or intensity is on the ordinate or Y-axis, and particle size is on the abscissa or X-axis). A bimodal particle size distribution refers to a collection of particles having two clearly discernable maxima on a particle size distribution curve, and a multimodal particle size distribution refers to a collection of particles having three or more clearly discernable maxima on a particle size distribution curve. A particle size distribution can refer to a particle size distribution for a collection of particles that is free of agglomerates. The polydispersity of a group of particles can be determined using DLS analysis. As the particles in a given sample approach uniform diameter, the polydispersity approaches 0.

Drug-polymer Conjugates

The invention is based at least in part on the discovery that polymer and oligomer conjugates with drugs and/or other chemical species that can function as an initiator of ring-opening polymerization can be readily prepared in a single step polymerization synthesis. In the synthesis, the chemical species initiator can be combined with one or more cyclic monomers and optionally, a ring-opening polymerization catalyst. In one embodiment, a nanoconjugate formation can be prepared using paclitaxel conjugated to PLA. The polymer and oligomer conjugates thus formed are useful in the preparation of particles, including microparticles and nanoparticles, having particle sizes that are useful for the delivery of the chemical species in vitro or in vivo. In some embodiments, nanoprecipitation methods can be used to form nanoparticles (nanoconjugates) containing the conjugates described herein. Nanoparticle nanoconjugates can be treated with PEG or an activated PEG-derivative to peglyate the surface of the nanoparticle. In other embodiments, the nano-conjugates can be treated with a PEG-containing block copolymer to coat the nanoconjugates by electrostatic interaction of the block copolymer and the surface of the nanoconjugates.

Polymer and oligomer conjugates described herein can be distinguished from conjugates formed by conjugation of a chemical species, particularly a drug, with a pre-formed polymer. The conjugates described herein can exhibit polymer average molecular weight much lower than pre-formed polymers. The conjugates described herein can also exhibit polydispersity much lower than pre-formed polymers. For example, polymer conjugates described herein can exhibit polydispersities of 1.5 or less, 1.3 or less, and/or 1.2 or less. In general the conjugates formed by the methods herein are more uniform in polymer length than those formed by conjugation of a chemical species with a pre-formed polymer.

Nanoconjugates (NCs) formed from nanoprecipitation of a polymer or oligomer conjugate described herein are distinguishable from nanoencapsulates (NEs) with respect to drug loading, drug encapsulation, drug release, particle distribution, as well as ease of manufacture. NEs typically exhibit low to medium drug loading (1-5 wt. %), which it is not possible to predetermine and which can vary from batch to batch. NCs exhibit predefined drug loading levels with much higher batch to batch consistency. NEs exhibit uncontrollable encapsulation efficiency (ranging 10-80%), which vary from batch-to-batch, and system-to-system and which are typically unable to encapsulate hydrophilic drugs. NCs exhibit approximately 100% encapsulation efficiency, with little or no batch-to-batch and system-to-system variation and they can be formed with both hydrophilic and hydrophobic drugs.

NEs typically exhibit significant burst release, with a 40-80% release in the first 24 hours. NCs exhibit little or no burst release of drug and provide for adjustable and controllable release of the drug. NEs usually exhibit multimodal particle distributions. NCs exhibit monomodal particle distribution. The manufacture of NEs involves a multi-component multi-step process that is difficult to scale up and which can be detrimental for long-term storage. Furthermore, it is difficult to remove unencapsulated drugs from NEs and the removal requires difficult to use filtration methods for sterilization. In contrast, the manufacture of NCs involves a single component system that is straightforward to scale up, and when properly stored, drug release is minimal or absent, increasing storage lifetime. Because there is essentially no free drug or drug aggregate to remove, the method is more efficient and less costly to implement.

During polymerization, a chemical species that functions for polymerization initiation (e.g., a drug that includes a hydroxyl moiety or a thiol moiety) becomes covalently bonded to one or more growing oligomer or polymer chains. The polymerization reaction can be a ring-opening polymerization reaction that has the characteristics of a living polymerization. The various initiators can be drugs and/or other chemical species having one or more hydroxyl groups or thiol groups that can function in the presence of a catalyst to initiate polymerization. The ring-opening polymerization can employ various cyclic monomers, including cyclic esters, cyclic carbonates, as well as cyclic siloxanes and cyclic phosphorous-containing monomers.

The polymerization can be exemplified by the polymerization of a lactide and/or glycolide and with a chemical species that is a drug and that possesses one or more hydroxyl or thiol groups. Numerous alcohol-metal oxides (RO-M) have been developed for controlled, living polymerization of lactide and other related cyclic monomers with quantitative, terminal conjugation of RO to polylactide through an ester bond. The amount of RO in the resulting polylactide can be precisely controlled by adjusting lactide/ROH ratio (e.g., the monomer to initiator molar ratio). The ROH can be a drug or other chemical species containing one or more hydroxyl groups that are to be conjugated to the polymer formed upon ring-opening polymerization. A number of organocatalysts, such as TBD (1,5,7-triazabicyclo[4.4.0]dec-5-ene) can be employed with hydroxyl or thiol containing initiators (i.e., drugs or other species to be conjugated) to form the conjugates described herein. The amount of the drug or other chemical species in the resulting polymer (or oligomer) can be controlled by controlling the monomer-initiator ratio. Any suitable catalyst that functions effectively in the presence of the drug of interest can be employed.

It was demonstrated that hydroxyl-containing chemotherapeutics can be quantitatively incorporated into polylactide using the polymerization method described herein (for example, using paclitaxel (Ptxl) and a Mg(II) complex ((BDI)MgN(TMS)$_2$ to activate Ptxl). A Zn(II) complex may also be employed. The drug release rate from the particle can be modulated by the cleavage of drug-polylactide ester bond, which is much more controllable than the diffusion of encapsulated non-covalently bonded drugs from a particle. Release kinetics of the drug can be controlled by adjusting drug loading and particle size. Because polymerization reactions can be controlled to give quantitative yield, drug loading can in turn be precisely controlled simply by adjusting monomer/drug (or other species) molar ratio (monomer to initiator ratio). The capability of these methods to precisely control drug loading by controlling the drug-polymer composition significantly enhances clinical translation of the nanoparticle products and the likelihood for regulatory approval of the nanoparticles for clinic use. Additionally, unprecedented high drug loading have been demonstrated (up to ~40%) with nanoparticles described herein.

Nanoparticle Formation and Use

Various species of nanoparticles (NPs) can be formed from polymer and/or oligomer conjugates described herein by various methods. In a specific embodiment, nanoprecipitation (NPP) can be employed where a solution of the conjugate is added to a solution in which the conjugate is insoluble. The precipitation step for forming nanoparticles employing the conjugates is simplified compared to the use of other starting materials because only one type of material, the conjugate, is involved. The precipitation and encapsulation of a free drug in a polymer, even in a binary system, in contrast, can be very complex. Control of integration of drug and polymer during phase separation is often poor, especially when these two elements have distinct chemical and physical properties. Biphasic particle distributions have been consistently observed in nanoencapsulates, which may be due in part to the self-aggregation of drug or polymers according to the like-dissolves-like principle. The methods described herein can provide particles with monomodal particle distributions.

The benefits described above for drug-polymer or drug-oligomer conjugates can be observed in the formation of conjugates with any chemical species that can function as a polymerization initiator and which is desired to be delivered in vivo in particulate form. Further, the specific benefits described above for the preparation of nanoparticle delivery compositions can be observed when the polymer or oligomer conjugates are employed to make any size particle that is useful for in vivo delivery.

The nanoprecipitation techniques can include dissolving the drug-polymer conjugates in a water-miscible solvent (e.g., THF or DMF) and adding to excess water. Diffusion of the organic solvent into water facilitates the formation of, for example, sub-100 nm sized nano-aggregates. Any of the many methods that are known in the art for preparing nanoparticles from polymer or oligomeric materials can be employed with the conjugates described herein.

In one aspect, the invention relates to a nanoconjugation technique which integrates drug-initiated cyclic ester (or carbonate) polymerization and nanoprecipitation to prepare drug-containing nanoparticles with pre-defined drug loading, near 100% encapsulation efficiency, minimized particle heterogeneity, and significantly reduced burst release effect. In applications for cancer chemotherapy, and particularly with nanoparticles useful in such therapy, particulate formulations can exhibit improved efficacy and decreased toxicity.

In an embodiment, the invention relates to polymeric nanoparticles for cancer treatment. In this aspect, the drug-polymer or drug-oligomer conjugate can include an anticancer agent or chemotherapeutic agent. Nanoparticles useful for cancer treatment may contain a mixture of conjugates with two or more different anticancer agents. Particulate formulations (e.g., those containing the NPs and NCs described herein) can be administered to a subject by any known method appropriate for the size of the particle, and appropriate for the therapeutic, diagnostic, or other agent carried in the particulate.

Drug-polymer conjugates can be used in the preparation of a medicament for in vivo delivery of the drug. The drug can, for example, be an anticancer agent. More specifically, the nanoconjugates can be used in the manufacture of a medicament for treatment of cancer. In specific embodiments, the medicament manufactured is in the form of particles, such as nanoparticles, for administration in any appropriate dosage form. In specific embodiments, the medicament further comprises a pharmaceutically acceptable carrier or diluent, for example, a carrier or diluent suitable for intravenous administration.

The term drug is used herein generically to include any chemical species that can provide therapeutic benefit to an individual in need of such benefit. Conjugates can be formed with appropriate drugs or other chemical species for delivery by a nanoparticle. At least one drug or other chemical species must have at least one functional group that can operate in the presence of a catalyst to initiate ring-opening polymerization. The functional group should be capable of interaction with the catalyst to form a species active for polymerization. Hydroxyl groups and thiol groups, for example, are suitable initiators of ring-opening polymerization. Hydroxyl and thiol groups can be primary, secondary, or tertiary functional groups. As is understood in the art, primary, secondary and tertiary hydroxyl and thiol group have different steric environments and can exhibit different relative reactivities.

In the description of chemical groups herein, the terms used are intended to have their broadest art-recognized meaning. The chemical species having at least one functional group functional for initiation of ring-opening polymerization can be combined with two or more cyclic monomers that can be polymerized by ring-opening polymerization and an appropriate ring-opening polymerization catalyst in an appropriate solvent under conditions and for a sufficient time to form oligomers or polymers as desired. The ability of a given chemical species to function for polymerization initiation can be readily assessed without undue experimentation in test polymerization reactions carried out employing materials and methods as described herein or as well-known in the art. The methods are further described in the Examples below.

Drugs containing hydroxyl groups that are useful in the preparation of drug-conjugates and nanoconjugate particles include doxorubicin, pamidronate, daunorubicin, epirubicin, mitoxantrone, bleomycin $A_2$, bleomycin $B_2$, vincristine, vinblastine, vinorelbine, vindesine, podophyllotoxin, etoposide, teniposide, paclitaxel, docetaxel, irinotecan, topotecan, abacavir, acyclovir, didanosine, darunavir (TMC-114), ribavirin, natamycin, fluconazole, posaconaczole, voriconazole, caspofungin, amphotericin B, and phenoxyethanol. Additional drugs that can be used in the nanoconjugates described herein and that have hydroxyl groups include, among others, tipranavir (TPV), saquinavir (SQV), ritonavir (RTV), indinavir, nelfinavir (NFV), amprenavir (APV), lopinavir (ABT-378), atazanavir (ATV), vinorelbine bitartrate, fulvestrant, sarcodictyins, camptothecins, bryostatin 1, (+)-cylindricine, (+)-lactacystin, aeruginosin 298-A, (+)-fostriecin, garsubellin A/hyperforin, (S)-oxybutynin, epothilone A, zidovudine (AZT), lamivudine (3TC), abacavir (ABC), and emtricitabine (FTC). Additional useful drugs include those having phenolic hydroxyl groups, which include among others include, bamethane, ethamivan, hexachlorophene, salicylanilide, pyrocatechin, thymol, pentazocine, phloroglucinol, eugenol, niclosamide, terbutaline, dopamine, methyldopa, norepinephrine, alpha-naphthol, polybasic phenols, adrenaline, phenylephrine, metaraminol, fenoterol, bithionol, alpha-tocopherol, isoprenaline, salbutamol, fenoterol, bithionol, chlorogenic acid and/or its esters, captopril, amoxicillin, betaxolol, masoprocol, genistein, daidzein, daidzin, acetylglycitin, equol, glycitein, iodoresiniferatoxin, SB202190, and tyrphostin SU1498.

Polymer Formation

For a given chemical species to be conjugated to a polymer, it may be necessary to perform trial polymerizations employing different catalysts. Some chemical species will be more compatible with organometallic catalysts, while others may be more compatible with organocatalysts. For example, the chemical species, even though containing appropriate functional groups, may not function (or may have limited function) to initiate polymerization with certain metal-based catalysts because the chemical species may deactivate the catalysts. Specifically, conjugation of PLA with mitoxantrone employing $(BDI)MgN(TMS)_2$ did not proceed, potentially because mitoxantrone deactivated the Mg catalyst.

Any of the cyclic monomers described herein, including AB2 type cyclic monomers, can be employed to form polymer or oligomer conjugates with such chemical species that can function for polymerization initiation. Any cyclic monomer or mixtures thereof that can be polymerized by ring-opening polymerization can be employed to form drug-conjugates and particles, particularly nanoparticles. In particular, cyclic monomers that can be polymerized by activated —OH, or a metal-oxide group, can be employed to form the drug-conjugates and particles. Useful cyclic monomers include cyclic esters and cyclic carbonates. Cyclic esters include lactones, cyclic diesters, and cyclic ester-amides, e.g., cyclic depsipeptides.

Cyclic esters can include compounds of Formula A:

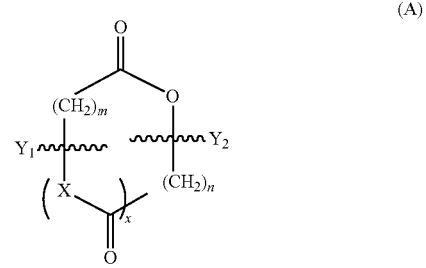

(A)

where m+n is 1-20, X is O or NH, x is 0 or 1 to indicate the presence of the ester or amide group, and $Y_1$ and $Y_2$ indicate the optional substitution of one or more carbon atoms of the ring with non-hydrogen substituents. Each $Y_1$ and $Y_2$, independently of one another, can be substituents that do not interfere with the polymerization reactions as described herein and can, for example, be hydrogen, halogen, —COOR, —NRR', —SR, —OR, where each R and R' are each independently hydrogen, alkyl (e.g., ($C_1$-$C_{10}$)alkyl), a guanidinium group, an imidiazole group, an alkenyl group (e.g., ($C_1$-$C_{10}$)alkenyl), an alkynyl group (e.g., ($C_1$-$C_{10}$)alkynyl), an aryl group (such as phenyl or naphthyl), an (aryl)alkyl group (e.g., benzyl or phenylethyl), or —$N_3$. Each $Y_1$ or $Y_2$ can also be an amino acid or a short peptide having 1-5 amino acids. Each $Y_1$ or $Y_2$ can also include groups as listed above that are protected with an art-recognized protecting group. Alkyl, alkenyl, alkynyl and aryl groups are optionally substituted with one or more halogens (e.g., —F, —Cl, —Br, and/or —I), —$N_3$, —COOR", —NR"R''', —SR", —OR" where R"

and R'" are each independently hydrogen or an unsubstituted alkyl, alkenyl, alkynyl or aryl group. In a specific embodiment, one or two of $Y_1$ and $Y_2$ can be a hydroxyl alkyl group. In specific embodiments, each $Y_1$ and $Y_2$ is hydrogen or an alkyl group having from 1 to 6 carbon atoms, for example, a methyl group.

Cyclic carbonates can include compounds of Formula B:

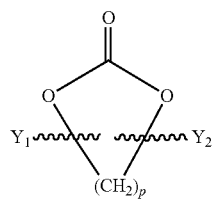

(B)

where p is 1-20, and $Y_1$ and $Y_2$ indicate optional substitution of one or more carbon atoms of the ring with non-hydrogen substituents, and where each $Y_1$ and $Y_2$ are as defined above. In specific embodiments, each $Y_1$ and $Y_2$ is a hydrogen or an alkyl group having from 1 to 6 carbon atoms, such as a methyl group. In a specific embodiment, one or two of $Y_1$ and $Y_2$ can be a hydroxyl alkyl group.

Cyclic esters include, but are not limited to, lactones such as β-butyrolactone (n=2), δ-valerolactone (n=4), ε-caprolactone (n=5), α-methyl-β-propriolactone, β-methyl-β-propriolactone, ω-pentadecalactone, ω-dodecalactone, or any lactide or glycolide, including all stereo-isomers thereof, such as SS-lactide, RR-lactide, RS-lactide, lactide-glycoloide, a substituted lactide or glycolide of Formula C:

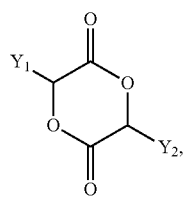

(C)

a cyclic depsipeptide (half-ester and half-amide) with 6 or 7 member ring structure, including, among others, Formulas D1-D3:

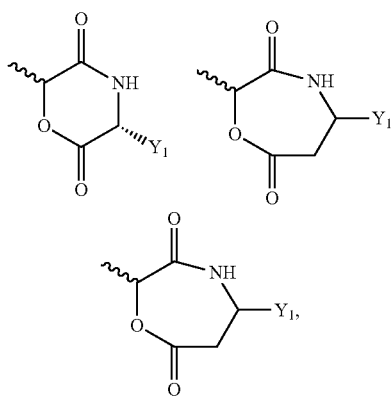

respectively.

Other cyclic monomers that are polymerizable by activated —OH or metal-oxide groups, include phosphorus-containing cyclic esters, including cyclic phosphates and phosphonates of Formula E:

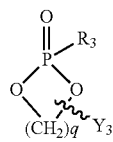

(E)

where q is 1 to 20, $Y_3$ is as defined for $Y_1$ and $Y_2$ above, and $R_3$ is $Y_3$ (phosphonates) or —$OY_3$ (phosphates).

Cyclic phosphonites can include compounds of Formula F:

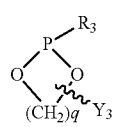

(F)

where variables are as defined above. Silicon-containing cyclic monomers can include compounds of Formula G:

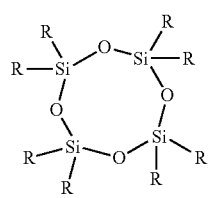

(G)

where each R is independently hydrogen or an optionally substituted alkyl group. In specific embodiments of the above cyclic monomers, each of $Y_{1-3}$ are hydrogen or alkyl groups having 1-6 carbon atoms. In specific embodiments of the above cyclic monomers, all $Y_{1-3}$ are hydrogen or all $Y_{1-3}$ are alkyl groups having 1-6 carbon atoms, for example, all $Y_{1-3}$ can be methyl groups. In specific embodiments of the above cyclic monomers, each R is hydrogen or an alkyl group having 1-6 carbon atoms. In specific embodiments of the above cyclic monomers, all R's are hydrogen or all R's are alkyl groups having 1-6 carbon atoms, for example, all R's can be methyl groups.

In specific embodiments, AB2 type cyclic polymerizable monomers are employed alone or in combination with other cyclic esters or cyclic carbonates. AB2 type cyclic ester monomers include those of Formula H:

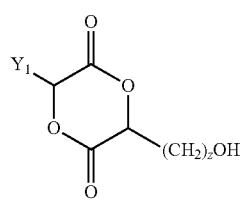

(H)

where z is 1 to 6 and $Y_1$ is as defined above. In specific embodiments, $Y_1$ can be hydrogen or an alkyl group having from 1-6 carbon atoms.

The polymerization reaction to form the drug-polymer nanoconjugates described herein can be carried out under various reaction conditions (temperature, solvent, concentrations) as is understood in the art. These conditions are in part selected to retain activity of the chemical species, such as the drug, that is to be conjugated. The polymerization reaction can be carried out in any appropriate solvent or mixture of solvents. In a specific embodiment, the solvent is an anhydrous, water-miscible solvent. The polymerization can be carried out in the same or a different solvent than that which is used in the later preparation of particles. Useful solvents for the polymerization reaction include, among others, THF, acetone, methylene chloride, chloroform, dimethylformamide, DMSO, acetonitrile, or mixtures thereof.

The nanoparticles described herein can successfully carry drug molecules or other chemical species to a desired in vivo location, e.g., a tumor site in a mammal. The drug can then enter cancer cells of a tumor. Systemically administered nanoparticles without suitable coating or modification are usually cleared rapidly from circulation and are localized predominately in the liver and spleen. Severe liver and spleen retention not only greatly diminishes the accessibility of the nanoparticles to target tissue, e.g., tumor tissue, but can also cause liver and spleen damage. Clearance is typically due to the scavenging by liver Kupffer cells and spleen macrophages. Nanoparticles without proper surface characteristics can be cleared within a few to tens of minutes by this passive and site-specific mechanism. In addition, nanoparticle surface characteristics and sizes play an important role in the blood opsonization, a process of the deposition of opsonins, like fibronectin, which can trigger immune responses and accelerate the clearance of nanoparticles from blood by macrophages. The binding of opsonins to the surface of nanoparticles can be substantially reduced when surface features of the nanoparticles are well controlled, for example, by the preparatory methods described herein.

Nanoparticle surface pegylation via electrostatic (non-covalent) interactions can reduce protein binding. The PEG layer forms a hydrophilic layer that can substantially reduce blood protein binding and reduce liver and spleen uptake. Pegylation creates stealth-like structures resembling the strategies developed by pathogenic microorganisms to bypass immune detection. Suppression of opsonization can thus be achieved and can be utilized to enhance passive retention of nanoparticles in circulation and to avoid trapping of nanoparticles in macrophages when they are in contact with blood. This simple strategy for manipulation of the nanoparticle surface can have a significant impact, as the circulation half-life of a nanoparticle can be increased from several minutes to several or tens of hours by this pegylation technique.

Nanoparticle size is another important parameter that can significantly affect the biodistribution and in vivo efficacy. Nanoparticle sizes can dramatically affect the clearance rate. Large particles with sizes above 200 nm are more likely to induce macrophage immune response and to activate the uptake by Kupffer cells than smaller nanoparticles. The size of fenestrae in the sinus endothelium in liver can be as large as 150 nm. Splenic filtration at interendothelial cell slits can predominate when particles size exceeds that of the cell slits (200-250 nm). Therefore nanoparticle sizes are usually controlled to 150 nm or below when they are to be used in anticancer drug delivery to prolong circulation.

The nanoparticle size should also not be too small, otherwise the particles can be very quickly filtered through the kidney (size<10 nm), which is a typical problem of polymer-drug conjugates with molecular weight of 40 kDa or lower. Very small particles (1-20 nm) can also slowly extravasate from the vasculature into the interstitial spaces, and are further accumulated in lymph nodes via lymphatic vessels. Nanoparticles with size smaller than 20 nm can readily escape from the vasculature into blood capillaries with open fenestration. Therefore, for some uses, nanoparticles should be large enough to prevent undesirable leakage from circulation, but should be small enough to minimize immune responses.

Nanoparticles used for anticancer delivery are typically in the range of 20 nm to 150 nm. To improve anticancer delivery, attention has been focused on the development of stealth technologies to provide means for increased extravasation of long circulating NPs at leaky tumor vasculature. The vasculature of tumors is highly heterogeneous. Depending on the specific location, tumor tissue can be vascularly necrotic or extremely vascularized so that adequate nutrient and oxygen can be transported to the tumor tissue to support its fast growth. Tumor blood vessels are also very heterogeneous and have several abnormalities when compared to normal blood vessels. In general, tumor blood vessels are leakier than their normal counterparts, and are shown to have a characteristic pore cutoff size ranging between 380 and 780 nm. These pores become the pathway for NPs to leave the circulation system and enter the tumor interstitial space. Therefore NPs with size of 150 nm or lower can freely diffuse through these leaky vessel pores, while particles with sizes larger than 400 nm are much less likely to extravasate into tumor issue. Because of the undeveloped lymphatic drainage system in tumor tissue, nanoparticles that extravasate the leaky pore of tumor vasculature cannot be readily removed. Therefore sustained circulation results in increased accumulation of nanoparticles over the time. This effect is the extremely well-known Enhanced Permeation and Retention (EPR) effect passive targeting mechanism in caner drug delivery.

The polymer and oligomer conjugates described herein can be chemically modified by reactions to introduce a desired terminal functional group. Terminal functional groups of interest for applications to drug delivery include among others, hydroxyl, thiol, amine, azide, alkyne, alkene, ketone, phenol, halide, imidazole, guanidinium, carboxylate, or phosphate groups. These functional groups can be introduced at the terminus of the polymers or oligomers herein employing well known chemical methods. The functional groups can be employed to further conjugate the polymer or oligomer conjugate of this invention with other chemical species, such as other polymers, other oligomers, carbohydrates, peptides, proteins, antibodies, nucleic acids, aptamers, and/or to provide sites for surface modification for nanoparticles prepared using the conjugates described herein.

The nanoconjugates can be multiple layer particles in which a particle described herein is treated to coat or otherwise provide an additional layer of polymer on the nanoparticle (e.g., the drug-polymer nanoconjugate). The additional polymer may be the same of different from that of the polymer of the polymer conjugate in the particle. Particles may contain two or more conjugated chemical species, e.g., two or more different drugs, that are compatible in a given application. Particles may contain different layers or portions in which the concentration of the chemical species or drug is different. For example an outer layer may contain a higher or lower concentration of a given chemical species (e.g., drug) compared to an inner layer. For example, an outer layer may contain PEG while an inner layer contains a conjugate of a different polymer. For example, a first inner layer can contain a polymer or oligomer conjugate of a first drug, and an additional outer layer containing a polymer or oligomer conjugate of a second drug. The additional outer layer may be added prior to or after the addition of the block copolymer coating, and an additional block copolymer coating may be added after the addition of the additional outer layer.

Nanoparticles can have a core/shell structure or have a multiple layer structure in which at least one of the core or shell or one of the multiple layers is a layer which is formed from the drug (or other chemical species)-polymer/oligomer conjugates. For example, the core of a nanoparticle can be formed form a polymer/oligomer conjugate by methods described above for forming nanoparticles. Thereafter a shell can be added to the core nanoparticle to generate a core/shell nanoparticle having increased particle size. More specifically, a core/shell nanoparticle can be formed with a core that is formed from a first polymer/oligomer conjugate and a shell that is formed from a polymer, e.g., a hydrophilic polymer or an amphiphilic polymer. In specific embodiments, the polymer can be an amphiphilic block co-polymer. In specific embodiments, the polymer is a polymer that is a PEG polymer or a polymer that comprises PEG blocks (as the polymer itself or as a block of a the polymer).

Alternatively, a core/shell nanoparticle can be formed from a first polymer/oligomer conjugate (to form the core) and a second polymer/oligomer conjugate to form the shell. Note that in some embodiments, one of the first or second polymer conjugates can have a label or reporter molecule (e.g., $^{99m}$Tc or the like) conjugated to the polymer or oligomer. In specific embodiments, the first and/or second polymer/oligomer conjugates can be selected from those of a taxane, an anthracycline antibiotic, or a Shh antagonist which has a functional group, such as a hydroxyl or thiol group that can function for polymerization initiation as described herein. In more specific embodiments, the first and/or second polymer/oligomer conjugates can be Ptxl, Dtxl, Doxo, cyclopamine, camptothecin, or a combination thereof.

Nanoparticles can be multiple layer nanoparticles containing three or more different layers wherein at least one layer is formed from a polymer/oligomer conjugate, including those of drugs or other chemical species, such as labels or reporter molecules. Nanoparticles include those having three, four or five layers. Nanoparticles include those in which all layers are formed from polymer/oligomer conjugates described herein. The nanoparticles can include those in which at least one layer is formed from a polymer/oligomer conjugate and at least one other layer is formed from a polymer.(non-conjugated polymer) such as a hydrophilic, hydrophobic or amphiphilic polymer. In specific embodiments, nanoparticles include those in which at least one layer is formed from a polymer/oligomer conjugate and at least one other layer is formed from an amphiphilic polymer comprising PEG, for example, LE5 or LE5L.

Polymers comprising PEG include, among others, amphiphilic copolymers comprising PEG such as poly(lactide)-PEG (PLA-PEG), an amphiphilic copolymer that has a PLA and PEG segment, and/or poly(glycolide-co-lactide)-b-methoxylated PEG (PLGA-mPEG), an amphiphilic copolymer that has a PLGA and PEG segment. In such copolymers, the PEG can, for example, range from 10% to 90%, from 20% to 50%, from 60% to 80%, from 50% to 75%, from 70% to 99% or from 1% to 50% of the copolymer.

Polymers and oliogmers used in the methods and materials herein are typically biocompatible and biodegradable (dependent upon the desired application). They typically exhibit little or no undesired toxicity in use.

The particles described herein can be surface-modified for preferential targeting to certain cell types. Preferential targeting of particles can, for example, be achieved by covalent or non-covalent attachment of targeting ligands to the surface of the particle.

The conjugates described herein are typically formed between a chemical species that has at least one hydroxyl group or one thiol group and oligomers or polymers formed by ring-opening polymerization. The chemical species typically contains at least one functional group that under the conditions of the reaction functions as an initiator of the polymerization. . The hydroxyl group can most generally be a primary (1'), secondary (2') or tertiary(3') hydroxyl group attached to a carbon, or a hydroxyl group attached to carbon of an aromatic ring that is generally described herein as a "phenolic hydroxyl group." Phenolic hydroxyl groups are those directly attached to a carbon of an aryl ring.

The terms hydroxyl and hydroxy are used interchangeable herein. Hydroxyl groups do not include the OH moiety of —COOH groups (carboxylic acid groups) in which the hydrogen of the group is acidic. The hydrogens of phenolic hydroxyl groups are more acidic than those of alcohols, but less acidic than those of carboxylic acid groups. The term hydroxyl as used herein also does not refer to —OH moieties which are bonded to N, P or S atoms. As is understood in the art, a primary hydroxyl group is a hydroxyl group bonded to a carbon atom that is also bonded to two hydrogens (e.g., —CH$_2$—OH). A secondary hydroxyl group is a hydroxyl group bonded to a carbon atom that is bonded to one hydrogen atom (e.g. —CH(M)—OH, where M is an atom or group other than H; in many cases M is a carbon containing group). A tertiary hydroxyl group is a hydroxyl group bonded to a carbon atom that is not bonded to a hydrogen; typically the carbon bonded to the hydroxyl group is bonded to three other carbon atoms. The thiol group can most generally be a primary (1'), secondary (2') or tertiary (3') thiol group attached to a carbon, where the terms primary, secondary and tertiary are used as defined for the hydroxyl groups.

As would be readily understood by one skilled in the art, when a drug is covalently bonded to a polymer through a hydroxyl or thiol group, the terminal hydrogen of the hydroxyl or thiol moiety is replaced by a bond to the polymer, thereby creating an ether or thioether linkage.

The particle formulations described herein can be used to treat various diseases, disorders or conditions. Treatment methods can include administering a therapeutically effective amount of a drug (e.g., in a drug-polymer nanoconjugate) to an individual in need of treatment.

Particulate formulations herein can, for example, be in the form of dry powders that can be rehydrated as appropriate. The particulate formulations can be in unit dosage forms, e.g., in capsules, suspensions, dry powders and the like. In such form, the formulation can be sub- divided in unit dose containing appropriate quantities of the active ingredient. The unit dosage forms can be packaged compositions, for example, packaged powders, vials, ampoules, prefilled syringes or sachets containing liquids. The unit dosage form can be, for example, a capsule, or it can be the appropriate number of any such compositions in package form.

The dosage employed can vary within wide limits and as is understood in the art can be adjusted to the individual requirements in each particular case. Any suitable form of administration can be employed in the method herein. The particles can be administered in oral dosage forms, intravenously, intraperitoneally, subcutaneously, or intramuscularly, all using dosage forms well known to those of ordinary skill in the pharmaceutical arts. Compositions can also be administered in intranasal form by topical use of suitable intranasal vehicles. For intranasal or intrabronchial inhalation or insulation, the compositions may be formulated into an aqueous or partially aqueous solution, which can then be utilized in the form of an aerosol.

The invention provides methods of treating disorders, diseases, conditions, and symptoms in mammals, such as humans, by administering to an individual in need of treatment or prophylaxis, a therapeutically effective amount of a particulate formulation described herein to the mammal in need thereof. The result of treatment can be partially or completely alleviating, inhibiting, preventing, ameliorating and/or relieving the disorder, condition or one or more symptoms thereof. Administration includes any form of administration that is known in the art to be effective for a given type of disease or disorder, and is intended to encompass administration in any appropriate dosage form. An individual in need of treatment or prophylaxis includes those who have been diagnosed to have a given disorder or condition and to those who are suspected, for example, as a consequence of the display of certain symptoms, of having such disorders or conditions.

Nanoparticle and Nanoconjugate Development

Much information has been accumulated in the last two decades for the control of the physicochemical properties of nanoparticles (NPs) and for the correlation of these properties with the in vivo biodistribution and antitumor efficacy of NPs. Although the ideal physicochemical properties of NPs for drug delivery applications have not been completely elucidated, a general consensus about important parameters of NPs, such as particle size, drug loading, loading efficiency, and release kinetics, that are critical to their in vivo applications, has been reached. The sizes of NPs should typically be less than 200 nm with narrow polydispersities to give satisfactory in vivo biodistribution. High drug loading, quantitative loading efficiency and controlled release profiles can be used for the in vivo applications of NPs.

Polylactide (PLA), a biocompatible and biodegradable material, has been used in the formulation of particles for biotechnology and drug delivery applications. NPs are typically prepared via nanoprecipitation of PLA and a drug. However, this conventional method tends to give NPs with various formulation challenges remaining to be addressed. For example, PLA/drug NPs typically show "burst" drug release profiles in aqueous solution. Typically as much as 80-90% of the encapsulated drug is rapidly released during the first few to tens of hours. The rapid drug release, also called dose dumping, can cause severe systemic toxicities.

Additionally, drug loading in conventional NPs can be very low, typically in a range of 1-5% for most NPs (Tong and Cheng, *Angew. Chem., Int. Ed.* 2008; 47:4830-4834). Drug loading of a delivery vehicle can be an important measure of its utility in clinic. At lower drug loadings, larger amounts of delivery vehicles are needed. Because of the limited body weight and blood volume of animals, the administration volumes are usually fixed. For instance, the volume of a solution intravenously administered to mice with 20-30 gram body weights should be controlled around 100 to 200 µL. Intravenous administration of NPs with 1% drug loading in a 100-µL solution at a dose of 50 mg/kg to a mouse with 20 g body weight requires the formulation of a concentrated, 1 g/mL NP solution. In practice, it is impossible to formulate such concentrated solutions and inject them intravenously. Furthermore, there is also a lack of general strategy to achieve quantitative drug encapsulation in PLA/drug NPs. Depending on the amount of drug being used, the hydrophobicity and hydrophilicity of drug, and the compatibility of drug and polymer, encapsulation efficiencies vary drastically in a range of 10% to 90%. Unencapsulated drugs can self-aggregate and can be difficult to be removed from the NPs. These formulation challenges significantly impact the processability and the clinical translation of PLA NP delivery vehicles to cancer therapy.

Controlled polymerization methodologies for preparing polyesters, polypeptides, and hydrocarbon based synthetic polymers with precisely controlled molecular weights and narrow polydispersities are well established, and these materials have been evaluated for use as drug delivery vehicles. However, controlled polymerization directly used in the formulation of drug delivery vehicles is rare. A new method that allows drug molecules to be incorporated into PLA via drug-initiated, controlled ring-opening polymerization of lactide (LA) has been developed and is described herein (FIG. 1a). Quantitative incorporation of paclitaxel (Ptxl) and other hydroxyl-containing therapeutic molecules have been incorporated to PLA via ester bonds facilitated by polymerization catalysts, such as the Zn-catalysts described herein.

When bulky chelating complexes are used, a Zn-catalyst can regulate the initiation and polymerization via the least sterically hindered 2'—OH of Ptxl (or a similar hydroxyl containing agent). This technique results in conjugates with precisely controlled composition and molecular weights. At a monomer/initiator (LA/Ptxl) ratio of 10, the drug loading of Ptxl-PLA conjugates and the NPs derived from the conjugates can be as high as 40% with nearly 100% loading efficiencies. Ptxl can be released in a controlled manner with negligible burst from these Ptxl-PLA conjugate NPs, referred to as nanoconjugates (NCs), to differentiate them from PLA/drug NPs prepared via encapsulation methods.

A comprehensive study of the formulation of Ptxl-PLA NCs, as well as the development of cancer targeting NCs by conjugating a cancer-specific targeting aptamer ligand to the surface of NCs, is described herein. It was demonstrated that Ptxl-PLA NCs can be co-precipitated with PLA-PEG-PLA, an amphiphilic triblock copolymer, directly in PBS to form NCs with diameters of 200 nm or less. These PEG-containing NCs are able to remain non-aggregated for an extended period of time in PBS. It was also discovered that albumin, an abundant protein in blood, can prevent NC aggregation during lyophilization. As a new lyoprotectant, albumin outperformed many well-known, saccharide-based lyoprotectants, such as trehalose and sucrose. NCs lyophilized in the presence of albumin can be reconstituted in PBS. NCs treated in such a manner then remain non-aggregated. These techniques allow for the formulation and handling of clinically applicable NCs with unprecedented simplicity. The techniques can therefore be applied broadly to the formulation of other polymeric NPs for drug delivery and cancer targeting.

Specific Embodiments

Described herein are novel nanoconjugates (NCs) that can be used as drug delivery vehicles. For example, a new, drug-initiated LA polymerization process was developed to allow for controlled drug incorporation to a terminal of PLA. In one embodiment, Ptxl can be conjugated to PLA regioselectively via its 2'—OH group (FIG. 1a). The resulting Ptxl-PLA conjugates have well controlled MWs and narrow polydispersities.

The capability of making Ptxl-PLA with controlled properties forms the foundation for further investigation of formulation parameters that are central to the clinical translation of polymeric NPs. It was demonstrated that Ptxl-PLA can be co-precipitated with PLA-PEG-PLA, an amphiphilic triblock copolymer, directly in PBS solution to form NCs that can remain non-aggregated in aqueous solutions, such as a salt solution. It was also discovered that albumin is an excellent lyoprotectant, which successfully provided a solid formulation of NCs that can be reconstituted with no NP aggregation, where the resulting particles have diameters of less than about 220 nm, or less than about 200 nm. The efficient targeting capability of NCs can be easily achieved by the straightforward conjugation of aptamers to the particle surface.

By incorporating the state-of-the-art lyoprotection technique described herein, it was demonstrated that polymer NCs containing a conjugated nucleic acid targeting ligand can be made into solid form in large quantities. The NCs in solid form can be reconstituted to well-dispersed NCs with no or negligible particle aggregation, with well-maintained targeting capability. The formulation strategies and the lyoprotection techniques described herein can be used for the controlled preparation of other polymeric nano-medicines for basic sciences as well as for clinical applications.

Accordingly, in one embodiment, Paclitaxel-polylactide (Ptxl-PLA) conjugate nanoparticles, referred to as nanoconjugates (NCs), can be prepared through Ptxl/(BDI)ZnN(TMS)$_2$-mediated controlled polymerization of lactide (LA), followed by nanoprecipitation. BDI is the acronym for 2-((2,6-diisopropylphenyl)-amido)-4-((2,6-diisopropylphenyl)-imino)-2-pentene. Nanoprecipitation of Ptxl-PLA resulted in sub-100 nm NCs with monomodal particle distributions and low polydispersities. The sizes of Ptxl-PLA NCs could be precisely controlled by using appropriate water-miscible solvents and by controlling the concentration of Ptxl-PLA during nanoprecipitation.

Co-precipitation of a mixture of PLA-PEG-PLA (PLA=14 kDa; PEG=5kDa) and Ptxl-PLA in PBS resulted in NCs that remained non-aggregated in PBS for an extended period of time. To develop solid formulations of NCs, a series of lyoprotectants were evaluated to identify formulations that effectively reduce or eliminate NC aggregation during lyophilization. Albumin was found to be an excellent lyoprotectant for the preparation of NCs in solid form, allowing lyophilized NCs to be readily dispersed in PBS without detectable aggregation. Aptamer-NCs bioconjugates were prepared and effectively targeted prostate-specific membrane antigen in a cell-specific manner, as described in the Examples below.

Preparation of Nanoconjugates

Useful particles can be prepared, for example, by known methods from solutions containing drug-polymer nanoconjugates described herein. The drug-polymer nanoconjugates can be formed during polymerization of the polymer or oligomer in which the drug is employed as an initiator of the polymerization of the monomers which form the polymer and/or oligomer. More specifically, the drug conjugates can be formed by ring-opening polymerization of cyclic monomers in the presence of an appropriate ring-opening polymerization catalyst and the initiator (the drug).

The particles are useful for drug delivery. The drug-polymer nanoconjugates generally range in size from about 2 nm to about 500 microns. In other more specific embodiments, the drug-polymer nanoconjugates are employed to make microparticles containing the drug and ranging generally in size from about 500 nm to about 100 microns. In other embodiments, the drug-polymer or drug-oligomer conjugates are employed to make nanoparticles containing the drug and ranging generally in size from about 55 nm to about 600 nm. In other embodiments, the drug-polymer or drug-oligomer conjugates are employed to make particles containing the drug and ranging generally in size from about 2 nm to about 100 nm. In other embodiments, the drug-polymer or drug-oligomer conjugates are employed to make particles containing the drug and ranging generally in size from about 200 nm to about 800 nm. In other embodiments, the drug-polymer or drug-oligomer conjugates are employed to make particles containing the drug and ranging generally in size from about 1 micron to about 500 micron.

In a specific embodiment, the methods of this invention can be employed to make nanoparticles in the 20-60 nm size range. Such nanoparticles can be made, for example by known micellation methods from polymer or oligomer conjugates as described herein followed by further reaction with a PEG-containing block polymer, for example, LE5 or LE5L.

In another specific embodiment, the methods of this invention can be employed to make nanoparticles in the 1-20 nm range that are particularly useful for delivery to cells. Such nanoparticles can be formed by employing cyclic AB2 type monomers or mixtures of such monomers with other cyclic esters and carbonate monomers described herein above. AB2 type monomers can polymerize to form hyperbranched or dendritic structures conjugated to a selected drug molecule. Particles formed directly by polymerization of the AB2 type monomers can be used for drug delivery. Alternatively, these particles can be subjected to surface treatments as discussed herein.

The drug-polymer nanoconjugates can include any small molecule drug (e.g., a small molecule drug that is a nonpeptide, non-sugar and non-nucleic acid-based drug). The drug can contain at least one functional group that can function for initiation of the ring-opening polymerization reaction, e.g. a hydroxyl group or a thiol group. The drug may contain, but need not contain, a plurality of such polymerization initiation groups, e.g., a plurality of hydroxyl groups or thiol groups. In preferred embodiments, the drug contains only one of such polymerization groups. The hydroxyl groups may be primary, secondary or tertiary hydroxyl groups. Similarly, the thiol groups may be primary, secondary or tertiary thiol groups. The hydroxyl group may also be a phenolic hydroxyl group. In specific embodiments, the drug contains one or more non-phenolic hydroxyl groups. In specific embodiments, the drug contains one or more non-phenolic hydroxyl groups which are primary or secondary hydroxyl groups. In specific embodiments, the drug contains a single nonphenolic hydroxyl group. In specific embodiments, the drug contains a single primary or secondary hydroxyl group. Exemplary drugs that can be employed in the polymers, compositions, and methods herein are described above.

In specific embodiments, the drug is hydrophilic and in related embodiments, the drug is water-soluble (e.g., exhibiting solubility in water in the range of mg/mL). In other specific embodiments, the drug is hydrophobic, and in related embodiments, the drug is not water-soluble or exhibits low water solubility (e.g., exhibiting solubility in water in the range of micrograms per mL or less).

In specific embodiments, the drug that is conjugated to the polymer or oligomer is a drug that is an anticancer agent or that is useful in chemotherapy. In specific embodiments, the drug is a taxane. In other specific embodiments, the drug is an anticancer agent of the anthracyclin family. In other embodiments, the drug is a protease inhibitor. In other specific embodiments, the drug is an inhibitor of reverse transcriptase. In other specific embodiments, the drug is an antiviral agent. In other specific embodiments, the drug is an antifungal agent. In other specific embodiments, the drug is a phenolic drug, i.e., having one or more phenolic hydroxyl groups. In other specific embodiments, the drug is a thiol drug, i.e., having one or more thiol groups.

The nanoconjugates, compositions, and methods described herein are also useful for delivery of drugs that are peptides, proteins, sugars and/or nucleic acid (DNA or RNA). In each case, the drug typically contains at least one functional group that can function as an initiator in the ring-opening polymerization reaction, e.g., at least one hydroxyl or one thiol group.

The nanoconjugates, compositions, and methods described herein can be more broadly applied to any molecule or other chemical species (including synthetic, or naturally-occurring molecules and organic or inorganic species), for example, that contains at least one functional group which can function as an initiator in a ring-opening polymerization reaction (e.g., a hydroxyl group or a thiol group) and that one wishes to administer or deliver in vivo using a particulate delivery system, such as a microparticle or a nanoparticle. The nanoconjugate may include any such useful chemical species including, without limitation, reagents for diagnostic methods, nutrients or vitamins (which may also be considered drugs in certain embodiments), or reporter molecules (e.g., radiolabeled or fluorescently labeled molecules). The chemical species to be conjugated to the polymer or oligomer may be hydrophilic, hydrophobic, water-soluble or water-insoluble. The chemical species may contain a plurality of hydroxyl groups or thiol groups that may be primary, secondary or tertiary hydroxyl groups and that may be phenolic hydroxyl groups. In specific embodiments, the hydroxyl groups are primary or secondary hydroxyl groups. In specific embodiments, the hydroxyl groups are phenolic hydroxyl groups. In specific embodiments, the thiol groups are primary or secondary thiol groups. In specific embodiments, the chemical species is a chemical species other than a saccharide. In specific embodiments, the chemical species is a chemical species other than a carbohydrate.

In specific embodiments, particles, such as nanoparticles, can exhibit drug loading (or more generally, loading of the selected chemical species) that is 20% or more, 30% or more, 40% or more, or 50% or more.

In specific embodiments, particles, such as nanoparticles, can exhibit long circulation lifetimes useful for effective in vivo delivery. This is particularly the case when the particles are surface modified employing methods described herein or employing methods that are known in the art. In specific embodiments, the particles can exhibit stability in salt solutions. The methods of forming the conjugates can be combined with any known method for the formation of particles, including nanoprecipitation, micellation, emulsion, and double emulsion methods.

The nanoconjugates can in general be those with any chemical species that it is desired to deliver in a particulate delivery system. For example, the drug can be an anticancer or chemotherapeutic drug. In specific embodiments, the conjugates are those in which the polymer of the conjugate on average has 100 or fewer monomer units. In other embodiments, the conjugates are those in which the polymer of the conjugate has on average 75, 50, or 25 monomer units. In specific embodiments, the conjugates are those in which the polymer has weight average molecular weight of 5000 or less, 2500 or less, 1500 or less, or 1000 or less. In specific embodiments, the chemical species of the conjugate can be conjugated or bonded to only one polymer or oligomer. In specific embodiments, the conjugate is conjugated or bonded to only one polymer or oligomer and at only one site in the chemical species.

In specific embodiments, the invention provides polymer or oligomer conjugates to hydrophilic chemical species, such as hydrophilic drugs. In other specific embodiments, a hydrophobic chemical species, such as hydrophobic drug, is conjugated to the polymer.

The invention further provides particles, including microparticles and nanoparticles, comprising the polymer conjugates or oligomer conjugates that are useful for in vivo delivery of selected chemical species, such as one or more drugs, for example, one or more anticancer or chemotherapeutic agents. In specific embodiments, the particles, including micro particles or nanoparticles, are surface-modified by any means known in the art, for example, with one or more antibodies, with one or more nucleic acid molecules, e.g., aptamers, with one or more peptides or proteins, e.g., enzymes, with one or more polymers or oligomers, e.g., amphiphilic polymers, such as amphiphilic polymers containing PEG. Surface-modification of particles as is known in the art can facilitate targeting of particles to certain tissue, can facilitate entry of particles into cells or can enhance stability of the particle. For example, nanoparticles formed from polyesters, polycarbonates or mixtures thereof can be coated with hydrophilic polymers such as PEG or amphiphilic polymers containing PEG to enhance circulation lifetime of the nanoparticle.

In additional embodiments, the invention provides particles having a core/shell structure or having a multiple layer structure in which at least one of the core or shell or one of the multiple layers is a layer which is formed from the drug (or other chemical species)-polymer/oligomer conjugates. Nanoparticles can have a core/shell structures in which the core or shell is formed from a polymer/oligomer conjugate described herein. Nanoparticles can also be formed with a core that is formed from a first polymer/oligomer conjugate and a shell that is formed from (1) a polymer, e.g., a hydrophilic polymer or an amphiphilic polymer or (2) a second polymer/oligomer conjugate. In specific embodiments, the first and second polymer/oligomer conjugates can be selected from those of a taxane, an anthracycline antibiotic, or a Shh antagonist which has a functional group, such as a hydroxyl or thiol group that can function for polymerization initiation as described herein. In more specific embodiments, the first and second polymer/oligomer conjugates can be selected from those of Ptxl, Dtxl, Doxo, cyclopamine, or camptothecin. Multiple layer nanoparticles containing three or more different layers wherein at least one layer is formed from a polymer/oligomer conjugate can be prepared. Nanoparticles include those having three, four or five layers.

Nanoparticles include those in which all layers are formed from polymer/oligomer conjugates described herein. Nanoparticles also include those in which at least one layer is formed from a polymer/oligomer conjugate and at least one other layer is formed from a polymer (non-conjugated polymer) such as a hydrophilic, hydrophobic or amphiphilic polymer. In specific embodiments, nanoparticles include those in which at least one layer is formed from a polymer/oligomer conjugate described herein and at least one other layer is formed from an amphiphilic polymer comprising PEG.

The invention further provides kits for carrying out the polymerization reactions herein to form polymer or oligomer conjugates with a selected chemical species having at least one hydroxyl group. The kits can include one or more containers that in turn include one or more cyclic monomers and/or one or more ring-opening polymerization catalysts, and optionally include instructions for carrying out the polymerization reaction, instructions for making particles, one or more reagents or instructions for surface modification of particles, one or more solvents for carrying out the polymerization or for making particles, one or more control initiators, additional receptacles for carrying out the reaction, for forming particles or for carrying out surface modification. In specific embodiments, kits can include a plurality of different cyclic monomers useful for making conjugates with different oligomers or polymers. In some embodiments, kits can further contain one or more different chemical species having at least one hydroxyl group for forming conjugates.

Additional embodiments of the invention will be apparent on review of the following detailed description, examples and figures. Other useful information regarding nanoconjugates can be found in U.S. Patent Publication No. 2008/0248126 (Cheng et al.), which is incorporated herein by reference in its entirety.

Nanoconjugates and Nanoconjugate Compositions

As described above, the invention provides a drug-polymer nanoconjugate comprising a drug covalently bonded to a polymer, a block copolymer coating, and an albumin coating;

wherein the drug-polymer nanoconjugate comprises one or more drugs and one or more polymers, one or more drugs of the drug-polymer nanoconjugate is located at an initiation point of a polymer of the drug-polymer conjugate, one or more of the drugs include at least one hydroxyl or thiol moiety, and such drug is covalently bonded to the polymer at the location of a hydroxyl or thiol moiety of the drug;

the polymer of the drug-polymer nanoconjugate comprises monomers derived from cyclic esters, cyclic carbonates, cyclic phosphates, cyclic siloxanes, cyclic phosphazanes, or cyclic peptides or amino acids;

the block copolymer coating comprises PEG and lactide blocks;

the block copolymer coating is coated with an amount of albumin effective to at least substantially prevent aggregation of the drug-polymer nanoconjugate to other drug-polymer nanoconjugates.

The nanoconjugate can also include one or more cell-targeting agents covalently bonded to the surface of the drug-polymer nanoconjugate or to the block copolymer coating.

Nanoconjugates therefore can be surface-modified as is known in the art to improve their usefulness as drug delivery vehicles. The diameter of the combined drug-polymer nanoconjugate, block copolymer coating, and albumin coating, can be about 2 nm to about 300 nm, or about 20 nm to about 200 nm. The diameter of the combined drug-polymer nanoconjugate, block copolymer coating, and albumin coating, can therefore be less than about 300 nm, less than about 250 nm, less than about 200 nm, or less than about 150 nm. The mass of the combined drug-polymer nanoconjugate, block copolymer coating, and albumin coating, can be less than 2 wt. % of total drugs, less than 1.5 wt. % of total drugs, less than 1 wt. % of total drugs, less than 0.5 wt. % of total drugs, or less than 0.25 wt. % of total drugs that are not covalently bonded to a polymer.

The block copolymer coating can be one or more PLA-PEG diblock copolymers, one or more PLA-PEG-PLA triblock copolymers, or a combination thereof. The molecular weight of the PEG block of the block copolymer coating is about 400 to about 40,000. The molecular weight of the lactide block of the block copolymer coating is about 1,000 to about 250,000. For example, the PEG block of the block copolymer coating can be about 5,000, and the molecular weight of the lactide block of the block copolymer coating can be about 5,000 to about 50,000. The terminal groups of the polymer can be hydroxyl, thiol, amine, azide, alkyne, alkene, ketone, phenol, halides, imidazole, guanidinium, carboxylate, or phosphate groups.

The drug-polymer nanoconjugate can remain non-aggregated in the presence of other drug-polymer nanoconjugates for more than 24 hours when contacted with the other drug-polymer nanoconjugates in water or in an aqueous solution. The cell-targeting agent can be an aptamer.

The block copolymer coating can be non-covalently bonded to the drug-polymer nanoconjugate through electrostatic interactions, and/or a block copolymer coating can be covalently bonded to a layer of the drug-polymer nanoconjugate composition. The mass ratio of the drug-polymer nanoconjugate to the block copolymer coating can be, for example, about 0.5 to about 1.5, or about 0.75 to about 1.25. The albumin of the albumin coating can be a mammalian serum albumin, such as bovine serum albumin or human serum albumin.

The invention also provides a composition comprising a plurality of nanoconjugates described herein wherein the composition of nanoconjugates has a monomodal nanoconjugate particle size distribution. The molecular weight distribution of the drug-polymer nanoconjugates can be, for example, less than 1.1, less than 1.07, less than 1.06, less than 1.05, less than 1.04, less than 1.03, or less than 1.02. The nanoconjugates can remain non-aggregated, for example, when exposed to a PBS solution for more than 30 minutes.

The invention further provides a method for delivering the drug of a drug-polymer nanoconjugate to the surface or interior of a cell. The deliver can include contacting a cell with a drug-polymer nanoconjugate described herein, so that the drug-polymer conjugate associates with the cell for a period of time sufficient for the drug-polymer nanoconjugate to release the drug from the polymer, thereby delivering the drug to the surface or interior of the cell. The cell can be a prostate cancer cell, breast cancer cell, lung cancer cell, pancreatic cancer cell, or colon cancer cell.

The molar ratio of cyclic monomer to drug initiator can be, for example, about 5,000:1 to 2:1. The drug can be a hydroxyl-containing small organic molecule, a macromolecule, or a peptide, saccharide or nucleic acid.

The one or more of the drugs of the drug-polymer nanoconjugate can be, for example, doxorubicin, daunorubicin, epirubicin, mitoxantrone, bleomycin $A_2$, bleomycin vincristine, vinblastine, vinorelbine, vindesine, podophyllotoxin, etoposide, teniposide, paclitaxel, docetaxel, irinotecan, topotecan, abacavir, acyclovir, didanosine, darunavir (TMC-114), ribavirin, natamycin, fluconazole, posaconaczole, voriconazole, caspofungin, amphotericin B, phenoxyethanol, tipranavir (TPV), saquinavir (SQV), ritonavir (RTV), indinavir, nelfinavir (NFV), amprenavir (APV), lopinavir (ABT-378), atazanavir (ATV), vinorelbine bitartrate, fulvestrant, sarcodictyins, camptothecin, bryostatin 1, (+)-cylindricine, (+)-lactacystin, aeruginosin 298-A, (+)-fostriecin, garsubellin A/hyperforin, (S)-oxybutynin, epothilone A, zidovudine (AZT), lamivudine (3TC), emtricitabine (FTC), bamethane, ethamivan, hexachlorophene, salicylanilide, pyrocatechin, thymol, pentazocine, phloroglucinol, eugenol, niclosamide, terbutaline, dopamine, methyldopa, norepinephrine, alpha-naphthol, adrenaline, phenylephrine, metaraminol, fenoterol, bithionol, alpha-tocopherol, isoprenaline, salbutamol, chlorogenic acid or an alkyl ester thereof, captopril, amoxicillin, betaxolol, masoprocol, genistein, daidzein, daidzin, acetylglycitin, equol, glycitein, iodoresiniferatoxin, SB202190, tyrphostin SU1498, or a combination thereof. The nanoconjugate can be layered such that the particles has a drug concentration gradient. For example, the particles can have a multilayer structure with different drug concentrations or different types of drugs in different layers. At least one layer of the particles can be formed from the drug-polymer nanoconjugate.

The invention therefore also provides a covalent drug-oligomer or drug-polymer conjugate prepared by polymerizing one or more cyclic monomers selected from the group consisting of cyclic esters, cyclic carbonates, cyclic phosphates, cyclic siloxanes, cyclic peptides or amino acid derivative, or cyclic phosphazanes, in the presence of a drug the structure of which comprises one or more hydroxyl groups and a ring-opening polymerization catalyst wherein the drug comprising the one or more hydroxyl groups is the initiator of the polymerization reaction. The drug-oligomer or drug-polymer conjugate can be layered or modified as described herein.

The polymer can include 5000 or fewer repeating units of the ring-opened monomer. The polymer can also include 500 or fewer repeating units of the ring-opened monomer. The polymer can further include 50 or fewer repeating units of the ring-opened monomer. The polymer can also include 20 or fewer repeating units of the ring-opened monomer. The polymer (e.g., an oligomer) can alternatively include 10 or fewer repeating units of the ring-opened monomer.

The invention therefore provides a nanoparticle comprising a core/shell structure or a multiple layer structure. At least one of the core or shell or one of the layers can be a nanoconjugate as described herein. In some embodiments, the monomers can be, for example, lactides, glycolides, or a combination thereof.

The invention yet further provides a method for preparing particles for in vivo delivery of a chemical species, for example, that has at least one hydroxyl group or thiol group. The method can include (a) conducting ring-opening polymerization of one or more cyclic monomers selected from cyclic esters, cyclic carbonates, cyclic phosphate, cyclic silicone, cyclic peptides or amino acid derivative, or cyclic phosphazane, or a combination thereof in anhydrous, water-miscible solvent in the presence of the chemical species having at least one hydroxyl group as a polymerization initiator and a polymerization catalyst to form a covalent drug-oligomer or drug-polymer conjugate; and (b) forming particles comprising the drug-oligomer or drug-polymer conjugate ranging in size from 2 nanometers to 100 microns.

The invention additionally provides a covalent oligomer or polymer conjugate prepared by polymerizing one or more cyclic monomers selected from the group consisting of cyclic esters, cyclic carbonates, cyclic phosphates, cyclic siloxanes, cyclic peptides or amino acid derivative, or cyclic phosphazanes, in the presence of a chemical species the structure of which comprises one or more hydroxyl groups and a ring-opening polymerization catalyst wherein the drug comprising the one or more hydroxyl groups is the initiator of the polymerization reaction. In any embodiment, the chemical species can be, for example, a diagnostic reagent, a peptide, a saccharide, a carbonhydrate, an inorganic species, a contrast agent, a vitamin, a nutrient, a nucleic acid, an RNA molecule, an siRNA, or a DNA molecule.

Pharmaceutical Formulations

The nanoconjugates described herein can be used to prepare therapeutic pharmaceutical compositions. The nanoconjugates may be added to the compositions in the form of a salt or solvate. For example, in cases where nanoconjugates are sufficiently basic or acidic to form stable nontoxic acid or base salts, administration of the nanoconjugates as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The nanoconjugates described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The nanoconjugates described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Nanoconjugates may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active agent in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the nanoconjugates, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the nanoconjugates may be incorporated into sustained-release preparations and devices.

The nanoconjugates may be administered intravenously or intraperitoneally by infusion or injection. Solutions of the nanoconjugates or its salts can be prepared in water, optionally mixed with a nontoxic surfactant. Dispersions can be prepared in glycerol, liquid, polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars (e.g., glucose, mannitol, or the like), buffers, or sodium chloride. Prolonged absorption of the injectable compositions can be brought about by agents delaying absorption, for example, aluminum monostearate and/or gelatin.

Sterile injectable solutions can be prepared by incorporating the nanoconjugates in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, nanoconjugates may be applied in pure form in combination with a liquid. However, it will generally be desirable to administer the nanoconjugates to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a nanoconjugate can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508). Such dermatological compositions can be used in combinations with the compounds described herein.

Useful dosages of the nanoconjugates described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a nanoconjugate, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The nanoconjugates can be conveniently administered in a unit dosage form, for example, containing 5 to 1000 mg/m$^2$, conveniently 10 to 750 mg/m$^2$, most conveniently, 50 to 500 mg/m$^2$ of nanoconjugates per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The nanoconjugates described herein can be effective antitumor agents and have higher potency and/or reduced toxicity as compared to nanoencapsulated formulation. The invention provides therapeutic methods of treating cancer in a mammal, which involve administering to a mammal having cancer an effective amount of a nanoconjugate or composition described herein. A mammal includes a primate, human, rodent, canine, feline, bovine, ovine, equine, swine, caprine, bovine and the like. Cancer refers to any various type of malignant neoplasm, for example, prostate cancer, colon cancer, breast cancer, melanoma and leukemia, and in general is characterized by an undesirable cellular proliferation, e.g., unregulated growth, lack of differentiation, local tissue invasion, and metastasis.

The ability of a nanoconjugate of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Aptamer-coated Nanoconjugates

Materials, Methods, and General Experimental Details. D,L-Lactide (LA) was purchased from TCI America (Portland, OR), recrystallized three times in toluene and stored at −30° C. in a glove box prior to use. β-Diimine (BDI) ligand and the corresponding metal complex (BDI)ZnN(TMS)$_2$ were prepared by following the published procedures (*J. Am. Chem. Soc.* 2001; 123:3229-3238) and stored at −30° C. in a glove box. Anhydrous solvents were purified by passing solvents through alumina columns and kept anhydrous by storing with molecular sieves. Paclitaxel (Ptxl) was purchased from LC Laboratories (Woburn, Mass.) and stored at −30° C. in a glove box prior to use. Other chemicals were typically purchased from Sigma-Aldrich (St Louis, Mo.) and used as received.

The molecular weights (MWs) of PLA were determined on a gel permeation chromatography (GPC) equipped with an isocratic pump (Model 1100, Agilent Technology, Santa Clara, Calif.), a DAWN HELEOS 18-angle laser light scattering detector, or an Optilab rEX refractive index detector (Wyatt Technology, Santa Barbara, Calif.). The wavelength of the HELEOS detector was set at 658 nm. Size exclusion columns (Phenogel columns 100 Å, 500 Å, 10$^3$ Å and 10$^4$ Å, 5 μm, 300×7.8 mm, Phenomenex, Torrance, Calif.) used for the separation of PLA or Ptxl-PLA conjugates were serially connected on a GPC. THF (HPLC grade) was used as the mobile phase of GPC. HPLC analysis was performed on a System Gold system (Beckman Coulter, Fullerton, Calif.) equipped with a 126P solvent module, a System Gold 128 UV detector and an analytical pentafluorophenyl column (Curosil-PFP, 250×4.6 mm, 5 μ, Phenomenex, Torrance, Calif.). The UV wavelength for Ptxl analysis was set at 227 nm. The NMR studies were performed on a Varian UI500NB system (500 MHz). The sizes and polydispersities of PLA NCs were determined on a ZetaPALS dynamic light-scattering (DLS) detector (15 mW laser, incident beam=676 nm, Brookhaven Instruments, Holtsville, N.Y.). The lyophilization of NCs was carried out on a benchtop lyophilizer (Freezone 2.5, Fisher Scientific, Pittsburgh, Pa.).

Preparation and characterization of Ptxl-$LA_{100}$. In a glove box, Ptxl (8.5 mg, 0.01 mmol) was dissolved in anhydrous THF (2 mL). $(BDI)ZnN(TMS)_2$ (6.4 mg, 0.01 mmol) was added and allowed to react with Ptxl for 15-20 minutes. LA (144.0 mg, 1.0 mmol) in THF (1.2 mL) was added dropwise to the vigorously stirred mixture of Ptxl and $(BDI)ZnN(TMS)_2$. The polymerization was monitored using FT-IR by following the disappearance of the lactone band of LA monomer at 1772 $cm^{-1}$ or using $^1$H-NMR by monitoring the methine (—CH—) peak of LA around 5.2-5.0 ppm. After the polymerization was complete, an aliquot of the polymerization solution was analyzed using HPLC to quantify any unreacted Ptxl to determine the incorporation efficiency of Ptxl in the Ptxl-PLA conjugates. The resulting Ptxl-PLA conjugate prepared at a LA/Ptxl ratio of 100 (Ptxl-$LA_{100}$) was precipitated with ethyl ether (10 mL), washed with ether and methanol to remove the BDI ligand, dried under vacuum and characterized by GPC and $^1$H NMR. Complete removal of BDI from Ptxl-PLA was verified by TLC.

General procedure for the preparation of Ptxl-$LA_{100}$ NCs via nanoprecipitation. Ptxl-$LA_{100}$ conjugate in DMF (50 μL, 10 mg/mL) (or another water-miscible solvent, such as acetone) was added dropwise to a nanopure water solution (2 mL). The resulting NCs were analyzed by DLS after nanoprecipitation, collected by ultrafiltration (5 minutes, 3000×g, Ultracel membrane with 10,000 NMWL, Millipore, Billerica, Mass.), washed with water to remove DMF (or other organic solvent), and then analyzed by SEM.

Synthesis of PLA-PEG multiblock copolymer. PLA-PEG block polymers were synthesized by following the procedures described above for the preparation of Ptxl-$LA_{100}$, using $(BDI)ZnN(TMS)_2$ as the catalyst and PEG as initiator. To prepare PLA-PEG diblock copolymer and PLA-PEG-PLA triblock copolymer (LE5 and LE5L, respectively, Table 1), $mPEG_{5k}$-OH and HO-$PEG_{5k}$-OH were used as the corresponding initiators in the presence of $(BDI)ZnN(TMS)_2$.

TABLE 1

PEG and PEG-PLA copolymers*

| Abbreviation | Name | $M_n$ (×$10^3$ g/mol) | MWD |
|---|---|---|---|
| E5 | $mPEG_{5k}$-OH | 5.3 | 1.01 |
| LE5 | PLA-$mPEG_{5k}$ | 19.3 | 1.09 |
| LE5L | PLA-$PEG_{5k}$-PLA | 34.4 | 1.12 |
| | PLGA-$mPEG_{5k}$ | 18.3 | 1.41 |

*$M_n$ = number-average molecular weight; PDI = polydispersity index. Abbreviations of chemicals: $mPEG_{5k}$-OH = mono-methoxy poly(ethylene glycol) with a molecular weight of 5 kDa; PLA = polylactide; PLGA = poly(lactide-co-glycolide) (LA/GA = 50/50 molar ratio).

General Procedure. In a glove box, $mPEG_{5k}$-OH (50 mg, 0.01 mmol) in anhydrous dichloromethane (DCM, 300 μL) was mixed with a DCM solution of $(BDI)ZnN(TMS)_2$ (6.5 mg, 0.01 mmol, 50 μL). The mixture was stirred for 15 minutes. A DCM solution of LA (144 mg, 1 mmol, 2.88 mL) was added to the vigorously stirred $mPEG_{5k}$-OH/(BDI)ZnN$(TMS)_2$ solution. The mixture was stirred at room temperature (~23° C.) for 16 hours. The conversion of LA was determined by FT-IR by monitoring the lactone band at 1772 $cm^{-1}$. The resulting copolymer LE5 was precipitated with ethyl ether (10 mL), washed with ether and methanol/acetic acid (100/1 (v/v), 10 mL) to remove the BDI ligand, and dried under vacuum. Complete removal of BDI was confirmed by NMR, HPLC and TLC. After the organic solvent was evaporated, the resulting product (LE5) was dissolved in THF (10 mg/mL) and analyzed by GPC. LE5L was prepared and characterized similarly as LE5. The MWs and molecular weight distributions (MWDs) of both LE5 and LE5L were listed in Table 1.

Formation and characterization of Ptxl-$LA_{100}$/LE5 via sequential precipitation. A DMF solution of Ptxl-$LA_{100}$ conjugate (50 μl, 2 mg/mL) was added dropwise into a nanopure water solution (2 mL) to give the Ptxl-$LA_{100}$ NCs. LE5 ($M_n$=1.9×$10^4$ g/mol, 2 mg/mL, 100 μL) or $mPEG_{5k}$ (E5, 2 mg/mL, 100 4) in DMF was added dropwise to the Ptxl-$LA_{100}$ NCs. A concentrated PBS solution (10×, 228 μL) was added to the nanoprecipitation solution to make the final salt concentration equivalent to 1×PBS. The NC sizes were measured by DLS. To determine the stability of the NCs in PBS solution, the particle sizes were followed for 30 minutes by DLS.

Formation and characterization of Ptxl-$LA_{100}$/LE5 NC via co-precipitation (CPP). A DMF solution of Ptxl-$LA_{100}$ conjugate (12 mg/mL, 50 μL) was mixed with a DMF solution of LE5 (12 mg/mL, 50 μL). The mixture was then added dropwise to a vigorously stirred water solution (4 mL). The resulting NCs were analyzed by DLS.

Formation and characterization of Ptxl-$LA_{100}$/LE5L via co-precipitation. A DMF solution of Ptxl-$LA_{100}$ (8 mg/mL, 50 μL) was mixed with LE5L in acetone (8 mg/mL, 50 μL). The mixture was then added dropwise to a vigorously stirred water or PBS solution (4 mL). The resulting NCs were analyzed by DLS. The stability of the NCs in the PBS solution was followed for 10-30 min by DLS.

Lyophilization of PLGA-mPEG NPs in the presence of lyoprotectants. An acetone solution of PLGA-mPEG (5 mg/mL, 100 μL) was added dropwise into a vigorously stirred water solution (4 mL) containing the NCs to make the PLGA-mPEG NPs. A lyoprotectant was added to the vigorously stirred NC solution at the selected lyoprotectant/NC mass ratio (varying from 2 to 20). The solution was then lyophilized, reconstituted with 2 mL water and stirred for 5 minutes. The sizes of the resulting NCs were analyzed by DLS.

Lyophilization of Ptxl-$LA_{100}$/LE5L NCs in the presence of albumin. An acetone solution of Ptxl-$LA_{100}$ m g/mL, 50 μL) was mixed with an acetone solution of LE5L (4 mg/mL, 50 μL). The mixture was added dropwise to a vigorously stirred water solution (4 mL). The resulting NC solution was stirred for 6 hours in a fume hood to evaporate the acetone; the resulting NC solution was then analyzed by DLS. An aqueous solution of bovine serum albumin (BSA) (12 mg/mL, 500 μL) was added to the NC solution. The mixture was lyophilized for 16 hours at −50° C. The resulting white powder was reconstituted with nanopure water (2 mL) and followed by addition of a concentrated PBS solution (10×, 222 μL). The solution was stirred for 5 minutes at room temperature. The resulting NC solution was analyzed by DLS.

Conjugation of aptamer to Cy5-$LA_{50}$/PLA-PEG-COOH NCs. Cy5-$LA_{50}$ was prepared by following the reported procedure (Tong and Cheng, *J. Am. Chem. Soc.* 2009; 131:4744-

4754). Cy5-LA$_{50}$/PLA-PEG-COOH NCs (w/w=1/1, 1 mL, 1 mg/mL in DNase RNase-free water) were incubated with an aqueous solution of 1-(3-dimethylaminopropyl)-3-ethylcarbodimide hydrochloride (EDC) (400 mM, 200 µL) and N-hydroxysuccinimide (NHS) (100 mM, 200 µL) for 15 minutes at room temperature. The resulting NHS-activated NCs were reacted with 5'-NH$_2$-modified A10 PSMA aptamer (1 µg/µL in DNase RNase-free water, 50 µL). The resulting NC-aptamer bioconjugates were washed with ultrapure water (15 mL) by ultrafiltration (5 min, 1000×g, Ultracel membrane with 10,000 NMWL, Millipore, Billerica, Mass., USA). The aptamer-modified NCs were re-suspended (1 mg/mL in DNase RNase-free water) and were analyzed by fluorescence-activated cell sorting (FACS, BD FACScan™ Flow Cytometer) and fluorescence microscopy (Leica SP2 Laser Scanning Confocal Microscope).

Analysis of cellular uptake of Cy5-LA$_{50}$/PLA-PEG-COOH NC-aptamer bioconjugates by fluorescence microscope. LNCaP and PC3 cells were grown in chamber slides in RPMI medium 1640 and F-12 medium (American Type Culture Collection), respectively, supplemented with 100 units/mL aqueous penicillin G, 100 µg/mL streptomycin, and 10% FBS at concentrations to allow 70% confluence in 24 hours (i.e., 40,000 cells per cm$^2$). On the day of experiments, the medium was replaced with Opti-MEM medium (200 µL) containing Cy5-LA$_{50}$/PLA-PEG-COOH (w/w=1/1, 50 µg) NC or Cy5-LA$_{50}$/PLA-PEG-COOH NC-aptamer (NC-aptamer, 50 µg, 5 wt % of aptamer). The cells and NCs were co-incubated for 2-6 hours, after which the cells were washed with PBS (3×200 µL), fixed with 4% formaldehyde, counterstained with Alexa-Flour 488 Phalloidin (Invitrogen, Calif., USA), mounted and then analyzed on a Leica SP2 Laser Scanning Con focal Microscope at 40× magnification. The images were collected along the z axis with a 0.8-µm interval and reconstructed using the software provided.

Analysis of cellular uptake of Cy5-LA$_{50}$/PLA-PEG-COOH NC-aptamer bioconjugates by FACS. LNCaP and PC3 cells were grown in 24-well plates in RPMI medium 1640 and F-12 medium (American Type Culture Collection), respectively, supplemented with 100 units/ml aqueous penicillin G, 100 µg/mL streptomycin, and 10% FBS at concentrations to allow 70% confluence in 24 hours (i.e., 40,000 cells per cm$^2$). On the day of experiments, cells were washed with pre-warmed PBS and incubated with pre-warmed phenol-red reduced OptiMEM media for 30 minutes before the addition of the Cy5-LA$_{50}$/PLA-PEG-COOH (50 µg) NC or Cy5-LA$_{50}$/PLA-PEG-COOH NC-aptamer (50 µg, 5 wt % of aptamer). The cells were incubated for 4 hours at 37° C., washed with PBS (2×500 µL per well), and were subsequently treated with 0.25% trypsin with EDTA for 10 minutes. The cells were transferred to a 15-mL falcon centrifuge tube and centrifuged at 1200 rpm for 5 minutes followed by removal of the trypsin solution using a pipette. After the cells were washed with PBS (2×500 µL/well), they were fixed with 4% formaldehyde for 10 minutes at room temperature, washed with PBS (1×500 µL) and analyzed by FACS.

Results and Discussion

Figure 2:
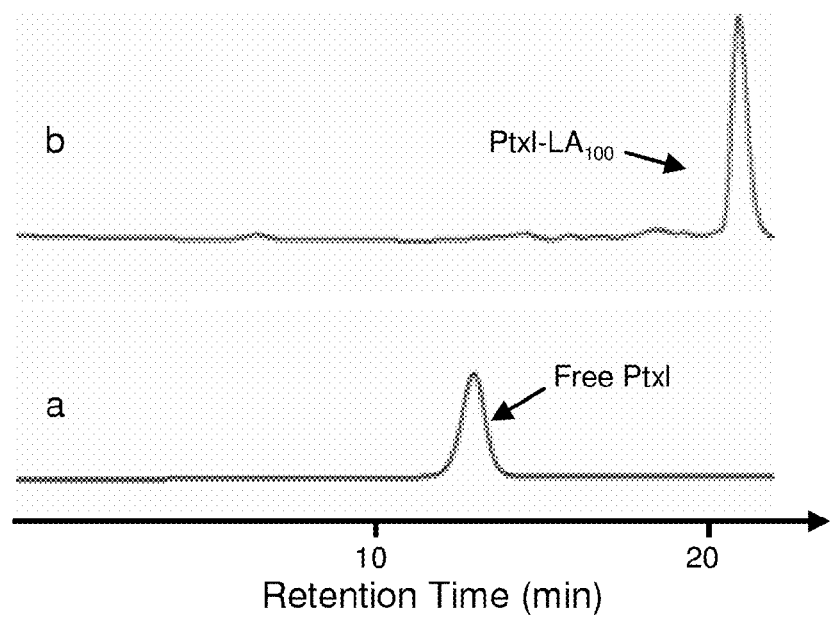
FIG. 2. HPLC spectrum of (a) free Ptxl and (b) a solution of Ptxl/(BDI)ZnN(TMS)$_2$-mediated LA polymerization at a LA/Ptxl ratio of 100. An aliquot (30-50 µL) of polymerization solution was injected into an HPLC equipped with an analytical RP-HPLC column (Curosil-PFP, 4.6×250 mm, 5 µ, Phenomenex, Torrance, Calif.). Mobile phase was acetonitrile/water with 0.1% TFA (50/50 (v/v)); the flow rate was set at 1.0 mL/min.

Synthesis of Ptxl-LA$_{100}$ nanoconjugates. To ensure a rapid and complete polymerization of LA at room temperature using Ptxl as the initiator, (BDI)ZnN(TMS)$_2$, an active catalyst developed by Coates and coworkers for the polymerization of LA (FIG. 1a), was used (Chamberlain et al., *J. Am. Chem. Soc.* 2001; 123:3229-3238). The regioselective initiation of Ptxl followed by controlled polymerization of LA was performed as previously by our laboratories (Tong and Cheng, *Angew. Chem., Int. Ed.,* 2008; 47:4830-4834). After Ptxl was mixed with 1 equiv. (BDI)ZnN(TMS)$_2$, the (BDI) Zn-Ptxl alkoxide formed in situ via the 2'—OH of Ptxl (FIG. 1a) initiated and completed the polymerization of LA within hours at room temperature, with nearly quantitative incorporation of Ptxl into the resulting PLA (trace ii, FIG. 2).

Figure 3:
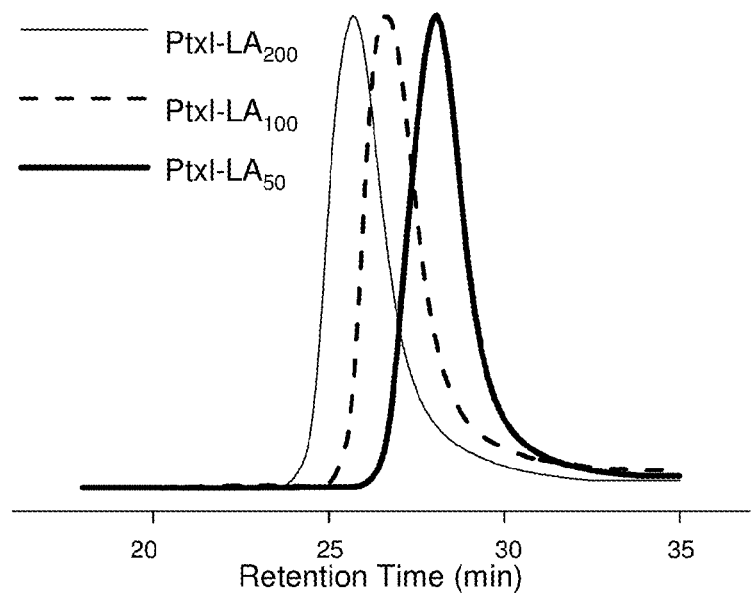
FIG. 3. GPC analysis of Ptxl-LA$_{200}$, Ptxl-LA$_{100}$ and Ptxl-LA$_{50}$.

Ptxl-LA$_{100}$ was prepared via Ptxl/(BDI)ZnN(TMS)$_2$-mediated LA polymerization at a LA/Ptxl ratio of 100. The obtained M$_n$ of Ptxl-LA$_{100}$ was 1.27×10$^4$ g/mol, which is in good agreement with the expected M$_n$ (1.52×10$^4$ g/mol). The Ptxl-LA$_{100}$ also had a very narrow molecular weight distribution (MWD, M$_w$/M$_n$=1.03) (FIG. 3), which was consistent with our previous observations for (BDI)ZnN(TMS)$_2$-mediated regioselective initiation of controlled LA polymerization with Ptxl. Ptxl-LA$_{50}$ and Ptxl-LA$_{200}$, the Ptxl-PLA conjugates prepared at a LA/Ptxl ratio of 50 and 200, respectively, were also synthesized using the same method with expected M$_n$'s and very narrow MWDs. The GPC traces of all three polymers showed monomodal molecular weight distribution patterns (FIG. 3).

Syntheses of Ptxl-PLA conjugates were straightforward. Gram-scale Ptxl-PLA conjugates with well-controlled composition (Ptxl linked to a PLA chain specifically through its 2'—OH group) and well-controlled MWs can be easily prepared using this drug-initiated polymerization method and utilized for the preparation of NCs. Ptxl-LA$_{100}$ is therefore a suitable candidate for development of controlled formulations for clinical translation of nanoparticulate drug delivery systems.

Formation of Ptxl-LA$_{100}$ nanoconjugates via nanoprecipitation (NPP). Nano-precipitation (NPP) can be used for the preparation of NPs with therapeutic agents embedded in the hydrophobic polymeric matrices. This method allows for rapid access to NPs in large quantity. Typically, a mixture of hydrophobic polymer and drug is dissolved in water-miscible organic solvent (e.g., DMF or acetone) and then added dropwise to a vigorously stirred water solution (V$_{water}$/V$_{solvent}$=10 to 40). The instantaneous diffusion of the organic solvent into water results in formation of polymer/drug NPs.

Figure 4:
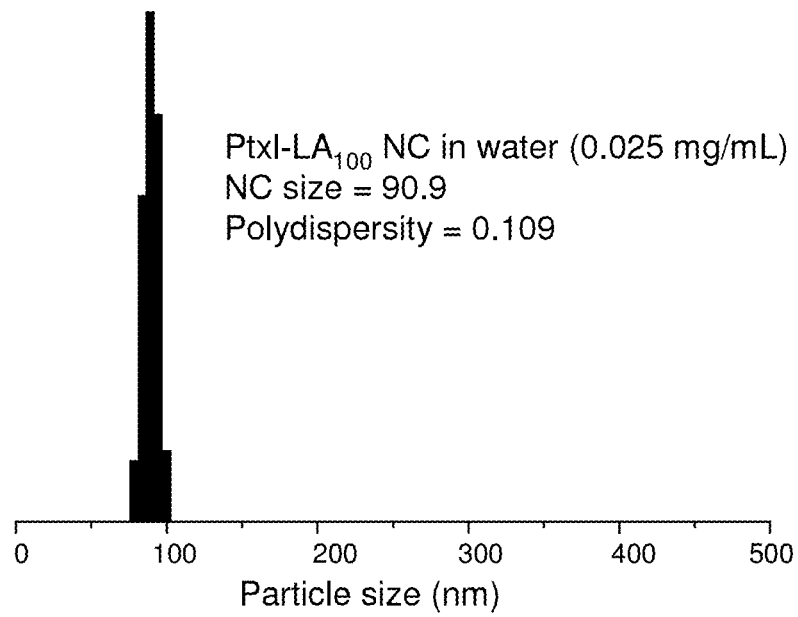
FIG. 4. Dynamic light scattering (DLS) analysis of Ptxl-LA$_{100}$ NC in water (0.025 mg/mL).

The NPP of Ptxl-LA$_{100}$ resulted in sub-100 nm Ptxl-LA$_{100}$ NCs with monomodal particle size distributions and low polydispersities (FIG. 4). In hundreds of NPP experiments performed using Ptxl-PLA conjugates with various MWs, NCs with more than one particle size distribution based on the DLS analysis were rarely observed. The narrow, monomodal particle size distributions for NCs derived from NPP of the Ptxl-PLA conjugates have also been confirmed by SEM analysis. The monomodal particle size distributions for NCs are in sharp contrast to the multimodal particle size distribution typically observed with NPs prepared by the co-precipitation (CPP) of a mixture of Ptxl and hydrophobic polymer (e.g., PLA or PLGA (poly(lactide-co-glycolide)) (Cheng et al., *Biomaterials* 2007;28:869-876). Because the multimodal distribution of NPs is due in part to the aggregation of the non-encapsulated drug molecules, the monomodal particle size distribution pattern observed and very low polydispersities with the Ptxl-LA$_{100}$ NCs can be attributed to the unimolecular structures of the Ptxl-PLA conjugates.

Control of Ptxl-LA$_{100}$ NC size in the NPP process (Approach i, FIG. 1b). Particle size is an important parameter of NPs, and size has a significant impact on biodistribution, clearance kinetics, and in vivo efficacy. With respect to biodistribution, the upper limit of desirable NP size is typically around 200 nm. Particles with diameters of 200 nm or greater are more likely to induce an immune response and be taken up by the Kupffer cells than their smaller counterparts, resulting in rapid clearance of particles from circulation. Particles 150 nm or smaller can escape through fenestration of the vascular endothelium and be cleared from circulation, while particles smaller than 10 and 30 nm are easily cleared through the kidney or lymph nodes, respectively. Although it is still not entirely clear which NP size leads toward the most favorable biodistribution and highest therapeutic efficacy in vivo when NPs are systemically administered, NPs diameters should typically be below about 200 nm.

Previous studies have revealed that NPs with diameters less than 200 nm can passively accumulate in solid tumor through the enhanced permeation retention effect (EPR), a mechanism that has been broadly utilized to improve the residence of NPs in tumor tissues. However, NPs with sizes below 200 nm may still behave dramatically differently in different size ranges in terms of their in vivo biodistribution, tumor targeting efficiency, tumor penetration and anticancer efficiency. Described herein are NCs with various size ranges to facilitate the evaluation of the correlation of the biodistribution and anticancer efficacy of NCs with NC size. Such information can be subsequently utilized for in vivo targeted cancer therapy. Also described herein are methods that allow for facile formulation of NCs with precisely-controlled sizes. A series of studies was performed using Ptxl-LA$_{100}$ as a PLA-drug conjugate to assess how solvent, concentration of Ptxl-LA$_{100}$, and surfactant would affect the sizes of NCs. Studies were also performed to determine how NCs can be prepared with no or negligible aggregation in PBS solution for an extended period of time to facilitate their in vivo applications.

Figure 5:
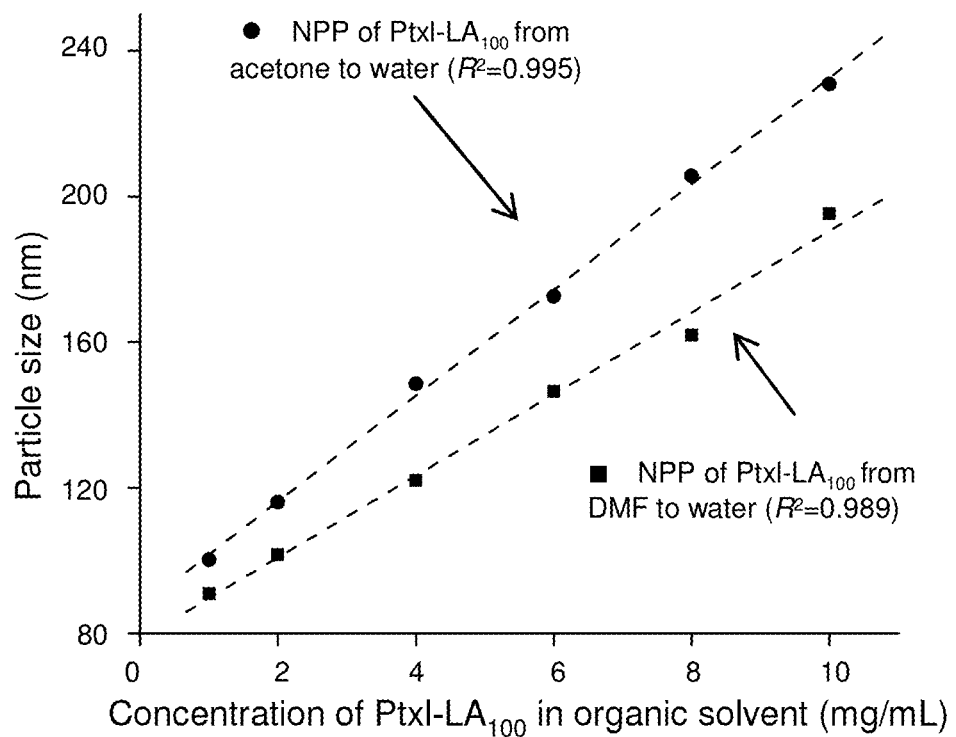
FIG. 5. Ptxl-LA$_{100}$ NC size versus the concentration of Ptxl-LA$_{100}$ with the use of acetone (●) or DMF (■) as the solvent for nanoprecipitation. The volume ratio of organic solvent to water was fixed at 1/40. The dashed line indicates the linear correlation of the NC size with the concentration of Ptxl-LA$_{100}$. $R^2$ is the linear correlation constant of the corresponding system.

The effect of solvent on the NPP of Ptxl-LA$_{100}$ with water as the non-solvent was first studied. The miscibility of the organic solvent with water can dramatically impact NP size in a given solvent/water system. As shown in FIG. 5, the sizes of Ptxl-LA$_{100}$NCs and the water-miscibility of the two organic solvents used were well correlated. An increase of water miscibility led to a decrease in the mean NC size when all other formulation parameters were held constant.

Ptxl-LA$_{100}$ NCs prepared with DMF as the solvent, a more water-miscible solvent, resulted in smaller particles. This can be due to more efficient solvent diffusion and polymer dispersion into water in this DMF/water NPP system. The Ptxl-LA$_{100}$ NCs prepared with acetone, a less water-miscible solvent than DMF, were typically 20-30 nm larger than the NCs prepared with DMF as the solvent at the corresponding concentration (FIG. 5). Acetone can be readily removed by evaporation because of its low boiling point. In contrast, DMF typically requires removal by ultrafiltration followed by extensive washing. Thus, NC formulation via NPP in the acetone/water system is much easier, which is more suitable for the large-scale preparation of NCs.

The effect of the Ptxl-LA$_{100}$ concentration during NPP on the size of NCs was then studied. When the polymer concentrations were varied during the NPP of Ptxl-LA$_{100}$ at a fixed solvent:water ratio (FIG. 5), a linear correlation of NC size with the Ptxl-LA$_{100}$ concentration was observed. The sizes of the NC increased from 90.9 nm to 195.3 nm as the polymer concentration in DMF increased from 1 mg/mL to 10 mg/mL. Similar correlation was also observed with acetone as the solvent for the NPP of Ptxl-LA$_{100}$ (FIG. 5). In both DMF/water and acetone/water NPP systems, the polydispersities of the NCs at all concentrations remained very low, ranging 0.061-0.128 and 0.081-0.168 for NCs derived from DMF/water and acetone/water system, respectively. Because of the linear correlation of NC size with the concentration of Ptxl-PLA conjugate during NPP, NCs with any desirable sizes ranging from 80 to 250 nm can be obtained simply by adjusting precipitation concentration.

Formation of NCs via sequential precipitation of Ptxl-LA$_{100}$ and LE5 (Approach ii, FIG. 1b). NCs were designed specifically for in vivo drug delivery applications. It is desirable to have NCs with prolonged circulation to maximize their therapeutic efficacy. To achieve protracted retention in circulation with reduced recognition by reticuloendothelial system, both the size and surface properties of NCs have to be well controlled. Systemically administered NPs without proper surface modification are usually cleared rapidly from the circulation and localized predominately in liver and spleen. Severe liver and spleen retention greatly diminishes the accessibility of the NPs to tumor tissues and can also cause liver and spleen damage. The clearance is typically due to scavenging by liver Kupffer cells and spleen macrophages. NP surface properties play a critical role in the blood opsonization, a process involving the deposition of protein opsonins that are recognized by phagocytic cells, thereby accelerating the clearance of NPs from blood. Opsonization of NPs can be substantially reduced when NP surface features are properly controlled. Modification of NP surfaces with PEG, referred to as "PEGylation", can reduce protein binding. Suppression of opsonization is thus achievable by PEGylation and can be to enhance the circulation half-life of NPs from several minutes to several or tens of hours.

Figure 6:
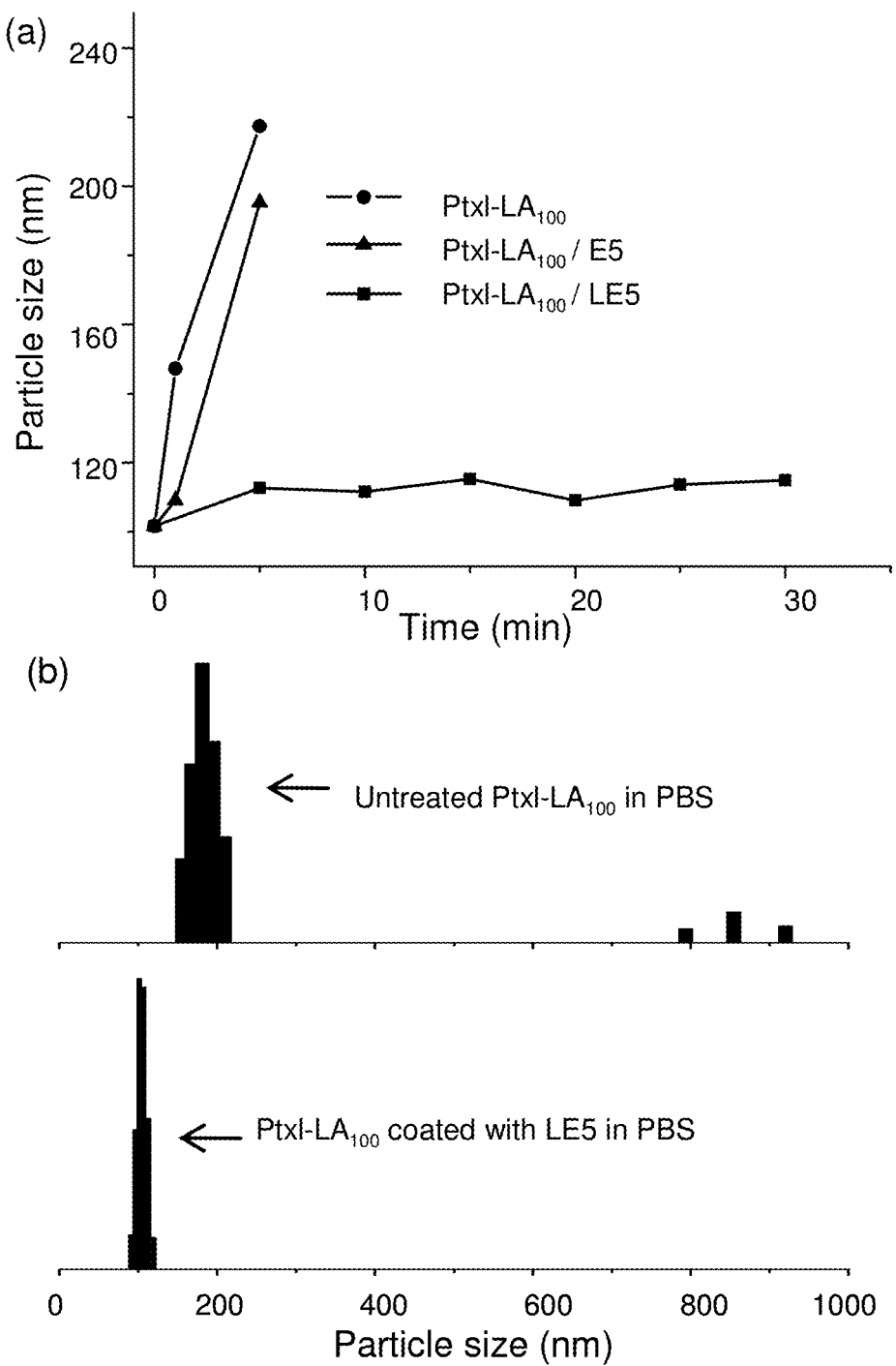
FIG. 6. (a) Stability of Ptxl-LA$_{100}$ NCs in PBS (1×) after coating with mPEG$_{5k}$ (E5) or with PLA-mPEG$_{5k}$ (LE5). (b) DLS spectra of Ptxl-LA$_{100}$/LE5 NCs and untreated Ptxl-LA$_{100}$NCs. Particle sizes were determined 4 minutes after particles were present in PBS solution.

Ptxl-LA$_n$ NCs have negative surface zeta-potential and remain non-aggregated in water due to surface charge repulsion. However, aggregation of NCs occurred in PBS, presumably due to salt-induced screening of the repulsive force (FIG. 6a). PEGylation strategies were thus adopted to create NCs with reduced or eliminated aggregation in salt solution. PEGylated NCs can also have reduced protein binding for in vivo applications.

PEG is typically covalently conjugated to the surface of NPs. To minimize efforts involved in conjugation chemistry, a direct deposition method to coat NC with PEG was developed. PLA-mPEG$_{5k}$ (LE5, Table 1), an amphiphilic block copolymer with PLA block of 14 kDa and mPEG segment of 5 kDa, was synthesized via the ring opening polymerization of LA using a mixture of mPEG and (BDI)ZnN(TMS)$_2$. Dropwise addition of LE5 to the Ptxl-LA$_{100}$ NC aqueous solution resulted in rapid coating of Ptxl-LA$_{100}$, via the hydrophobic interaction of PLA segment of LE5 and the hydrophobic NC surface. After treatment, the size of the Ptxl-LA$_{100}$ NC increased from 101.6 nm to 112.7 nm. The resulting NCs remained non-aggregated for at least 30 minutes in PBS (FIG. 6a).

To demonstrate the importance of the PLA block to the non-covalent surface PEGylation, we added mPEG5k (E5, Table 1) to the NC solution followed by the addition of PBS. Without the hydrophobic PLA block, E5 should not form stable interaction with NCs. As expected, Ptxl-LA$_{100}$/E5 NCs formed large aggregates almost instantaneously after PBS was added, following a very similar aggregation pattern as the parental NCs in PBS (FIG. 6a). Furthermore, analyses of the LE5 coated Ptxl-LA$_{100}$ NC by DLS before and after treatment showed that particles retained their monomodal distribution pattern (FIG. 6b). The DLS experiments indicated that LE5 favorably precipitated on the surface of Ptxl-LA$_{100}$ NCs instead of self-assembling to form micelles. The resulting PEG coated NCs form a core-shell nano-structure with hydrophobic polymer-drug conjugate being in the core and LE5 on the shell, which was confirmed by TEM studies.

Formation of NCs via co-precipitation of mixtures of Ptxl-LA$_{100}$ and LE5 (Approach iii, FIG. 1b). Formation of Ptxl-LA$_{100}$1LE5 core-shell type nanostructures can be performed in two steps: a NPP of Ptxl-LA$_{100}$ to form NC core followed by coating with LE5 to form a PEG shell. Preparation of salt-stable NCs in such a step-wise manner is difficult to handle, especially for the preparation of NCs on a large scale. It is desirable to formulate salt-stable Ptxl-LA$_n$ NCs in one step. Accordingly, the formulating salt-stable NCs by co-precipitating (CPP) a mixture of Ptxl-LA$_{100}$ and LE5 was evaluated.

Ptxl-LA$_{100}$ was mixed with LE5 at 1:1 mass ratio in DMF, a fixed ratio utilized throughout the following experiments. The mixture was then precipitated in nanopure water ($V_{DMF}/V_{water}$=1/40). Linear increase in particle size with the increase of polymer concentration was observed (FIG. 7a), following a similar trend as the NPP of Ptxl-LA$_{100}$ previously discussed for FIG. 5. The sizes of NCs gradually increased from 61.4 nm to 121.0 nm when the concentration of Ptxl-LA$_{100}$ increased from 2 mg/mL to 10 mg/mL. When acetone was used as the solvent, similar linear correlation of NC sizes with the concentration of Ptxl-LA$_{100}$ was observed. The sizes of NCs increased from 79.2 to 145.9 nm when the concentration of Ptxl-LA$_{100}$ increased from 2 mg/mL to 10 mg/mL. The NCs obtained in the latter case (CPP of Ptxl-LA$_{100}$/LE5 from acetone to water) were roughly 20-25 nm larger than the NCs prepared with DMF as solvent at corresponding concentrations, similar to the solvent effect described in FIG. 5.

Figure 7:
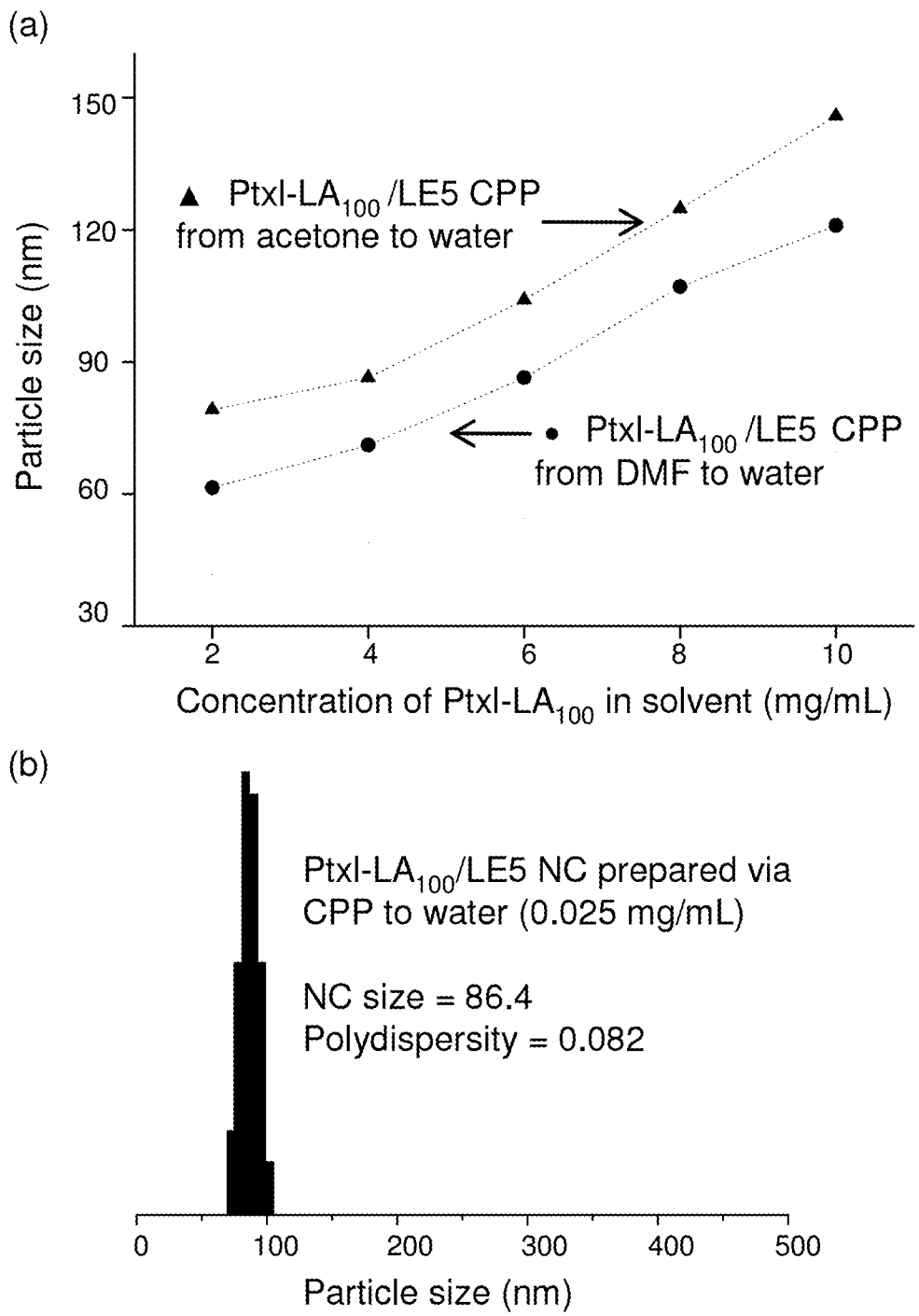
FIG. 7. (a) Co-precipitation (CPP) of Ptxl-LA$_{100}$/LE5 (wt/wt=1/1) from DMF or acetone solution into water at various Ptxl-LA$_{100}$ concentrations (DMF (or acetone)/water=1/40 (v/v)). (b) Ptxl-LA$_{100}$/LE5 NC size distribution determined by DLS. Conditions: Ptxl-LA$_{100}$ in DMF (50 µL, 12 mg/mL) was mixed with a DMF solution of LE5 (50 µL, 12 mg/mL). The mixture was added dropwise to a vigorously stirred water solution (4 mL). The resulting Ptxl-LA$_{100}$1LE5 NCs was analyzed by DLS.

NCs prepared in both DMF/water and acetone/water systems showed narrow-dispersed, monomodal particle size distribution, exemplified by the Ptxl-LA$_{100}$/LE5 NC prepared via the NPP with a concentration of 6 mg/mL in acetone (FIG. 7b). The stability of the NCs in PBS was then evaluated. After precipitating a mixed DMF solution of Ptxl-LA$_{100}$ and LE5 (Ptxl-LA$_{100}$=4 mg/mL) in a water solution ($V_{DMF}/V_{water}$=1/40) followed by the addition of PBS to the resulting NC solution, the particles remained non-aggregated for an extended period of time based on the DLS analyses.

Figures 8, 9:
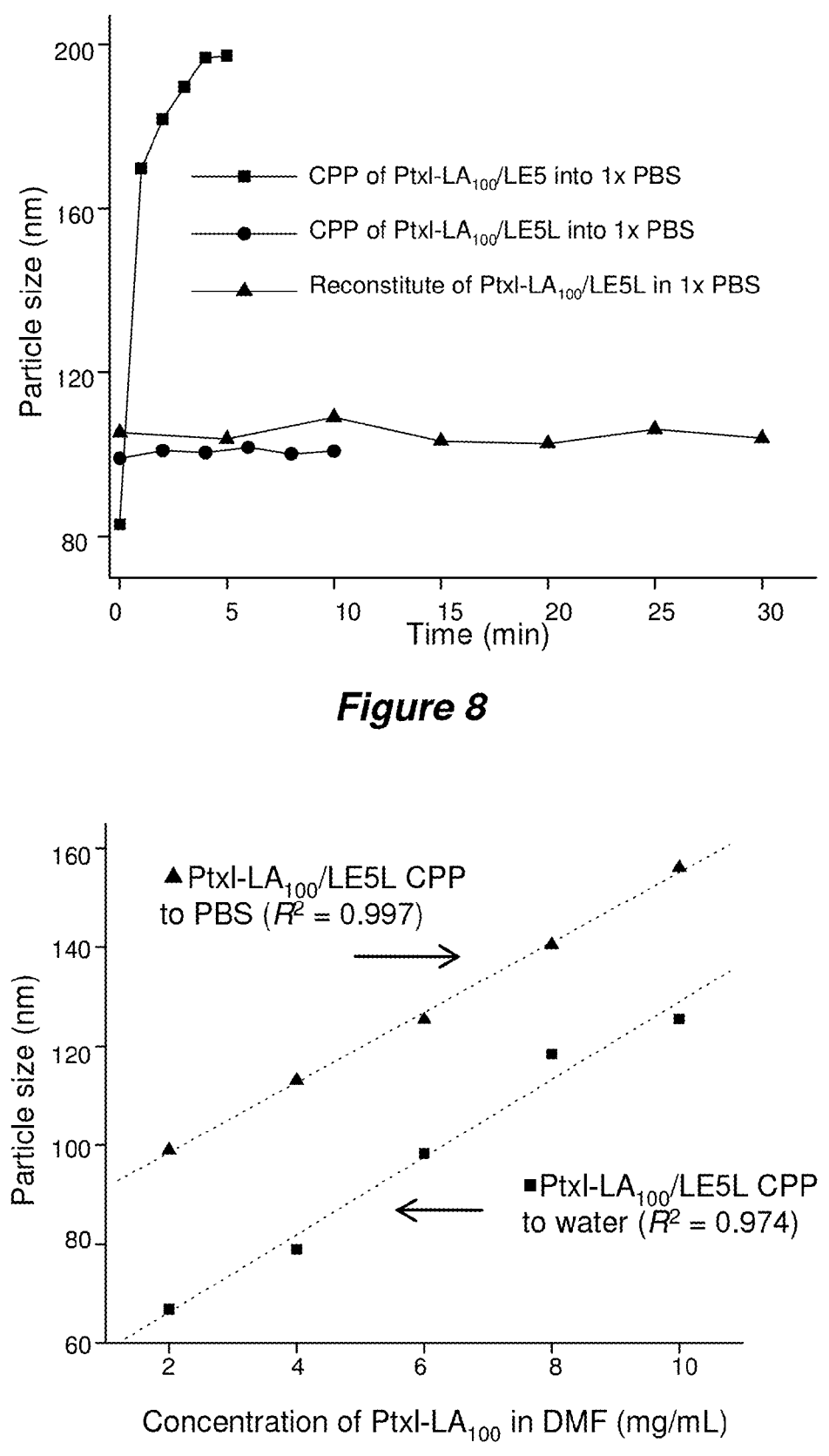

Formation of NCs via co-precipitation of mixtures of Ptxl-LA$_{100}$ and LE5L (Approach iv, FIG. 1b). To further simplify NC formulation, it was determined whether it was possible to formulate stable NCs directly in PBS solution. When a mixture of Ptxl-LA$_{100}$ and LE5 was directly co-precipitated in PBS, the resulting NCs were not stable in PBS and formed large aggregates rapidly (FIG. 8). The particle size increased from 83 nm to 197 nm within 6 minutes. Interestingly, when LE5L (Table 1), a ABA type triblock copolymer with PEG as the B clock (MW=5 kDa) and PLA as the A block (MW=14 kDa), was mixed with Ptxl-LA$_{100}$ at 1:1 mass ratio in DMF and subsequently precipitated in PBS, the resulting Ptxl-LA$_{100}$/LE5L NCs were found to be surprisingly stable in PBS and remained non-aggregated for an extended period of time (FIG. 8).

To compare the non-solvent effect on the NC formulation, CPP of Ptxl-LA$_{100}$/LE5L was conducted at various concentrations in both PBS and water. When water was used as the non-solvent, the size of the Ptxl-LA$_{100}$/LE5L NC gradually increased from 66.8 nm to 125.5 nm as the concentration of the mixture increased from 2 mg/mL to 10 mg/mL. CPP of the Ptxl-LA$_{100}$ and LE5 mixture in water or to PBS showed a linear correlation of Ptxl-LA$_{100}$ concentration with NC size (FIG. 9), similar to the NPP of the Ptxl-LA$_{100}$ in water reported previously (FIG. 5). When the CPP was performed with PBS as the non-solvent, the sizes of NCs were typically 20-40 nm larger than those derived from the NPs prepared with water as the non-solvent and followed a linear trend with the concentration of Ptxl-LA$_{100}$. The sizes of NCs increased from 99.0 to 156.5 nm when the concentration of the of Ptxl-LA$_{100}$ in the mixture increased from 2 mg/mL to 10 mg/mL (FIG. 9). NCs prepared at various concentrations all stayed non-aggregated in PBS for an extended period of time.

Triblock LE5L and diblock LE5 self-assemble in different manners. LE5 forms star-like micelles, while LE5L, because of its ABA type of amphiphilic structure, tends to form flower-like micelles (FIG. 1b). Hydrophobic polymer chains in flower-like micelles tend to have stronger interaction than those in star-like micelles, which may contribute to the formation of Ptxl-LA$_{100}$/LE5L NCs with stably coated PEG shell and enhanced stability in the PBS solution.

Lyophilization and Storage of Ptxl-PLA NCs. Formulations of small-scale NPs that stay non-aggregated in PBS for in vitro or in vivo laboratory studies are relative easy to control. However, in order to facilitate their clinical translation, NPs have to be prepared in large quantity with well controlled properties, which need to remain unchanged during the processes of manufacturing, storage and transport prior to their use in clinic. In Ptxl-PLA, because Ptxl is covalently conjugated to PLA through an ester bond that is subject to hydrolysis upon exposure to water, handling of NCs in aqueous solution in the abovementioned processes is undesirable. NCs typically must to be formulated in solid form in order for them to be used clinically.

PLA-based NPs tend to aggregate during lyophilization. As expected, when the Ptxl-LA$_{100}$/LE5 or the Ptxl-LA$_{100}$/LE5L NCs with sub-100 nm sizes were lyophilized, reconstituted and re-analyzed by DLS, micrometer-sized, non-dispersible aggregates were observed. Administration of polymeric NPs with micron size aggregates via tail vein injection led to instantaneous mice death.

There have been many studies using lyoprotectants to physically separate NP from aggregating during lyophilization. Mono- or di-saccharides, such as sucrose, dextrose, maltose, sorbitol, glucose, are frequently used as lyoprotectants because their biocompatibility and low cost (Musumeci et al., *J. Nanosci. Nanotechnol.* 2006; 6:3118-3125). Studies on the lyophilization of PLGA-mPEG$_{5k}$ NPs with the use of sucrose as the lyoprotectant were conducted in our labs (*Biomaterials*, 2007; 28:869-876). Although the aggregation of PLGA-mPEG$_{5k}$ NPs was reduced during lyophilization, formation of substantial amount of large, non-dispersible aggregates was still observed. A large number of lyoprotectants were therefore screened using PLGA-mPEG$_{5k}$ based NPs. These lyoprotectants were compared with sucrose for their capabilities of preventing NP aggregation during lyophilization (Table 2).

TABLE 2

Characterization of PLGA-mPEG NPs Lyophilized in the Presence of Various Lyoprotectants and Reconstitution by Water.$^a$

| Lyoprotectant$^b$ | $W_C/W_{NP}$$^c$ | Size in nm (STD)$^d$ | PDI (STD)$^d$ | Distr. No.$^e$ | $S_L/S_O$$^f$ | Aggr.$^g$ |
|---|---|---|---|---|---|---|
| Sucrose | 2 | 245.2 (2.1) | 0.227 (0.003) | 2 | 3.93 | Y |
| Sucrose | 10 | 217.5 (3.0) | 0.220 (0.002) | 2 | 3.49 | Y |
| Sorbitol | 2 | >1000 | >1000 | N.D. | N.D. | Y |
| Sorbitol | 10 | 764.8 (39.2) | 0.299 (0.021) | 2 | 12.28 | Y |
| Maltose | 2 | >1000 | >1000 | N.D. | N.D. | Y |
| Maltose | 10 | 220.4 (3.2) | 0.288 (0.008) | 2 | 3.54 | Y |
| Dextrose | 2 | 250.4 (9.5) | 0.345 (0.0120) | 2 | 4.02 | Y |
| Dextrose | 10 | 79.1 (2.3) | 0.075 (0.032) | 2 | 1.26 | Y |
| Mannose | 2 | >1000 | >1000 | N.D. | N.D. | Y |
| Mannose | 10 | 245.2 (1.6) | 0.254 (0.011) | 2 | 3.93 | Y |
| Galactose | 10 | >1000 | >1000 | N.D. | N.D. | Y |
| Glycine | 10 | >1000 | >1000 | N.D. | N.D. | Y |
| SDS | 10 | >1000 | >1000 | N.D. | N.D. | Y |
| BSA | 2 | 511.8 (24.7) | 0.392 (0.005) | 2 | 8.21 | Y |

TABLE 2-continued

Characterization of PLGA-mPEG NPs Lyophilized in the
Presence of Various Lyoprotectants and Reconstitution by Water.[a]

| Lyoprotectant[b] | $W_C/W_{NP}$[c] | Size in nm (STD)[d] | PDI (STD)[d] | Distr. No.[e] | $S_L/S_O$[f] | Aggr.[g] |
|---|---|---|---|---|---|---|
| BSA | 6 | 175.9 (3.3) | 0.343 (0.008) | 1 | 2.82 | N |
| BSA | 10 | 114.1 (1.4) | 0.110 (0.002) | 1 | 1.83 | N |

[a]PLGA-mPEG$_{5k}$ ($M_n$ = 19.4 × 10$^3$ g/mol) was used to study the efficiency of lyoprotectant. The original PLGA-mPEG NP had a diameter of 62.7 nm, which was formulated through the NPP of PLGA-mPEG to water. After the NPP was complete, the corresponding lyoprotectant was added at the selected lyoprotectant/NP mass ratio prior to lyophilization.
[b]SDS = sodium dodecyl sulfate; BSA = bovine serum albumin.
[c]$W_C/W_{NP}$ = the mass ratio of lyoprotectant chemicals vs. NP.
[d]PDI = polydispersity; STD = standard deviation.
[e]Distr. No. = the number of particle size distributions. N.D. = not determined.
[f]$S_L/S_O$ = the ratio of the lyophilized NP size to pre-lyophilized NP size.
[g]Aggr. = visible large aggregates; Y = aggregates observed; N = no aggregates observed.

PLGA-mPEG$_{5k}$ NPs were prepared via nanoprecipitation of PLGA-mPEG$_{5k}$ (Table 1) as previously described (*Biomaterials*, 2007; 28:869-876). Standard saccharide-based lyoprotectants, such as sucrose, sorbitol, maltose, dextrose and mannose, were able to reduce NP aggregation to some degree when the NPs were lyophilized along with these lyoprotectants (Table 2). High lyoprotectant chemical/NP mass ratio ($W_C/W_{NP}$) was found to be more effective in terms of reducing NP aggregation. However, even at a $W_C/W_{NP}$ ratio as high as 10, significant NP aggregations were observed in all saccharide-based systems.

DLS analyses of these NPs after lyophilization showed multimodal particle size distributions. Some large, non-dispersible aggregates precipitated from the solution and were even visible with the naked eye. Other sugars, such as galactose, could not prevent NP aggregation at all, even at a lyoprotectant/NC mass ratio of 10. Amino acids (e.g., glycine) and surfactants (e.g., SDS) were also evaluated as the lyoprotectant and it was found that they were unable to prevent NP aggregation during lyophilization (Table 2).

Because none of the small molecules tested could effectively prevent NP aggregation during lyophilization, macromolecules were evaluated to potentially provide better lyoprotection during NP lyophilization. Bovine serum albumin (BSA) was evaluated as a lyoprotectant of NPs. At a BSA/NP mass ratio of 2, the NP size increased by 8.2 times from 62 nm before lyophilization to 512 nm after lyophilization. Two particle size distributions were observed. When the BSA/NP mass ratio increased to 6 and 10, the size of the lyophilized NP became 176 nm and 114 nm, respectively. This corresponds to roughly 2.8× and 1.8× the pre-lyophilized NPs. The use of albumin allowed for completely dispersed lyophilized NPs with sub-200 nm diameters with absolutely no precipitates. The reconstituted NPs showed monomodal particle size distribution as determined by DLS.

Figure 10:
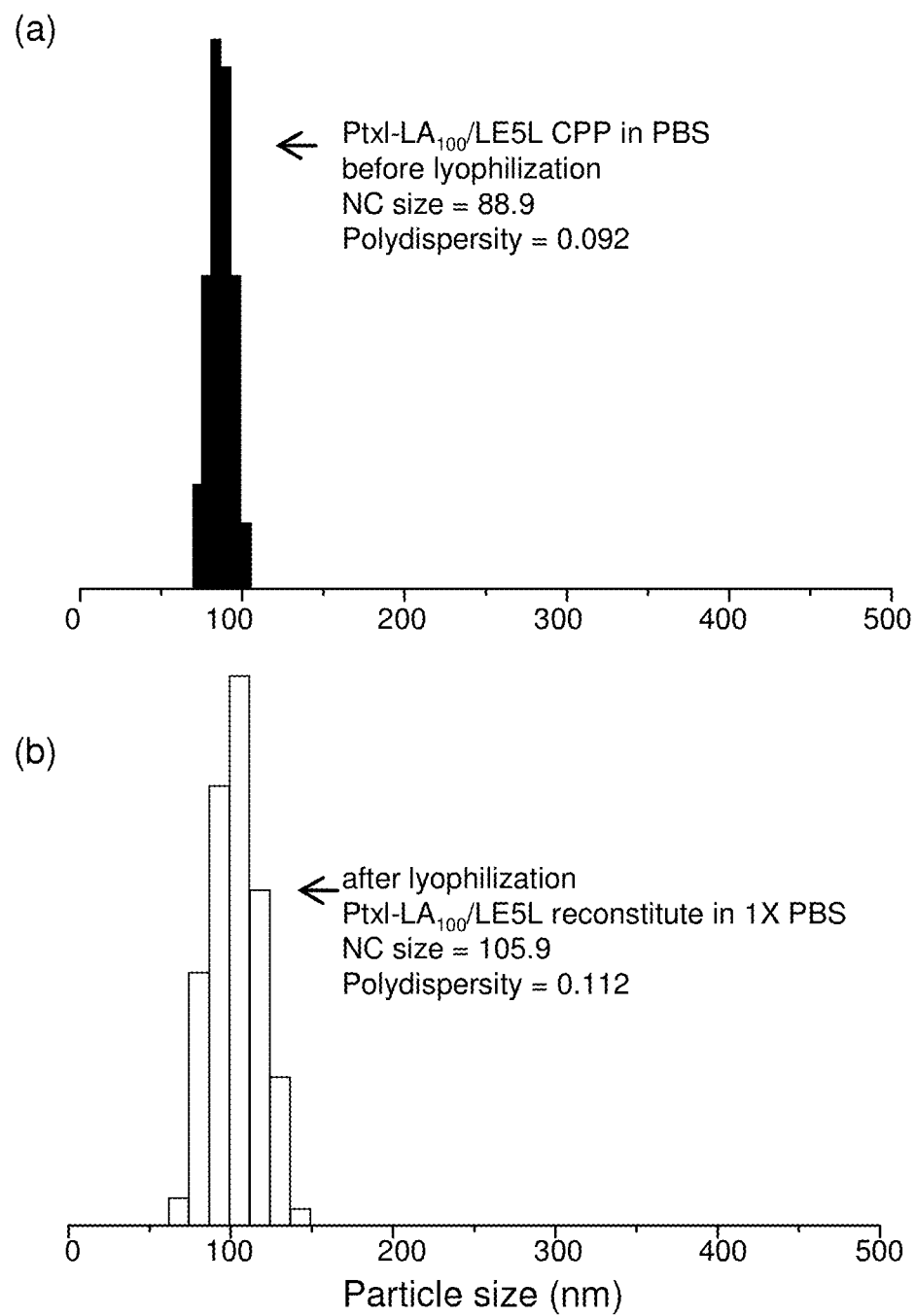
FIG. 10. (a) DLS spectrum of NC obtained from the co-precipitation of an acetone solution of Ptxl-LA$_{100}$JLE5L (w/w=1/1, Ptxl-LA100=2 mg/ml, 100 µL) in water (4 mL, acetone/water=1/40 (v/v)). The obtained NC had a diameter of 88.9 nm with a polydispersity of 0.092. (b) The resulting NC solution was then mixed with an aqueous solution of BSA (500 µL, 12 mg/mL) and the mixture was lyophilized for 16 hours at −50° C. The resulting powder was reconstituted with 2 mL of water followed by the addition of a concentrated PBS solution (222 µL, 10×). The mixture was stirred for 5 minutes at room temperature and analyzed by DLS. The obtained NC had a diameter of 105.9 nm with a polydispersity of 0.112.

Albumin was then evaluated for stabilizing Ptxl-LA$_{100}$/LE5L NC. A Ptxl-LA$_{100}$/LE5L NC was first prepared by co-precipitation as described previously for FIG. 9. The particles size and the polydispersity of the resulting NC were 88.9 nm and 0.092, respectively, as determined by DLS (FIG. 10(a)). After lyophilization at a BSA/NC mass ratio of 15 followed by reconstitution with 1×PBS, the NC size increased slightly to 105.9 nm (FIG. 10(b)) but remained non-aggregated for at least 10 minutes during the course of DLS analysis. Monomodal particle size distribution was verified by DLS analysis. The polydispersity of NCs remained as low as 0.112. This experiment was repeated multiple times with consistent and highly reproducible results, and with no NC aggregation in each of the repeated experiments. Because of the biocompatibility of albumin, this albumin-based lyoprotection strategy can be broadly used in solid formulations for drug delivery or other translational applications.

Ptxl-PLA NCs for prostate cancer targeting. Aptamers are either single-stranded DNA or RNA that specifically bind to a target ligand or ligands. The aptamers used herein were selected from a library of nucleic acids with random sequences via a combinatorial process called Systematic Evolution of Ligands by Exponential Enrichment (SELEX). When used for cancer targeting, aptamers are capable of binding to target antigens, with extremely high affinity and specificity in a manner resembling antibody-mediated cancer targeting. Aptamers are typically non-immunogenic and exhibit remarkable stability against pH, temperature and solvent. Synthesis of aptamers is a chemical process and thus shows negligible batch-to-batch inconsistency. These exceptional properties of aptamers are in sharp contrast to antibodies that are typically unstable against temperature and pH change, are immunogenitic, and have significant batch-to-batch variability.

An A10 aptamer with 2'-fluoro-modified ribose on all pyrimidines and a 3'-inverted deoxythymidine cap was identified via SELEX and utilized to target extracellucular prostate-specific membrane antigen (PSMA). The A10 aptamer binds to PSMA-positive LNCaP prostate cancer cells but not PSMA-negative PC3 prostate cancer cells. PLGA-A10 aptamer bioconjugates are also capable of targeting LNCaP cells in vitro and in vivo.

Cy5 (a fluorescence dye with hydroxyl groups) was used to initiate LA polymerization to prepare Cy5-PLA and subsequently Cy5-PLA NCs for study of the in vitro cancer targeting (Tong and Cheng, *J. Am. Chem. Soc.* 2009; 131:4744-4754). The amine-terminated A10 aptamer was conjugated to the PLA-PEG-COOH/Cy5-PLA NCs (particle size 132.8 nm with the polydispersity of 0.031) through the carboxylic acid-amine coupling reaction in the presence of EDC and NHS to give aptamer/PLA-PEG-COOH/Cy5-PLA NCs (aptamer-Cy5 NC). After purifying the aptamer-Cy5 NCs by centrifugation and washing the NPs with PBS, it was found that the size of aptamer-Cy5 NCs increased slightly to 157.1 nm with a polydispersity of 0.144 after conjugation of the A10 aptamer.

Freshly prepared aptamer-Cy5 NCs were then applied to the LNCaP (PSMA+) and PC-3 (PSMA-) cells, and their binding and internalization were assessed by fluorescence-activated cell sorting (FACS) flow cytometry. The mean fluorescence intensity of the LNCaP cells (PSMA+) incubated with aptamer-Cy5 NC for 4 hours was 376.7 (arbitrary intensity unit on FACS Cy5 channel), as compared to 72.4 for PS3 cell (PSMA-) and 16.4 in the untreated LNCaP cells. The fluorescence intensity of the aptamer-Cy5 NC treated LNCaP cells was 5.2 times higher than that of PC-3 cells treated under the same condition, indicating enhanced aptamer-Cy5 NC binding to PSMA+LNCaP cells and potentially improved NC internalization.

A kinetic study for the internalization of aptamer-Cy5 NCs into LNCaP cells was then performed. The LNCaP cells treated with aptamer-Cy5 NCs for 2 hours revealed a mean fluorescence intensity of 136.2, as compared to 16.4 of the untreated cells. When the LNCaP cells were treated with aptamer-Cy5 NCs for 6 hours, the mean fluorescence intensity increased to 779.8, indicating 5.7 times more NCs were internalized into the cells. Those observations were confirmed by an uptake imaging study using confocal microscopy. The uptake of Cy5 NCs to LNCaP cells was significantly enhanced when NCs were coated with aptamer.

Incubation of aptamer-Cy5 NCs with LNCaP cells for longer time resulted in substantially increased NC internalization. Because PC3 cells do not express the PSMA protein, there was essentially no difference between the aptamer-Cy5 NC and the Cy5 NC without aptamer with respect to their capability of cell-binding and internalization. Incubating PC3 cells with NCs for longer time resulted in slightly increased NC uptake. The binding of aptamer-Cy5 NCs to the PC3 cells was substantially weaker than to LNCaP cells. These in vitro studies demonstrated that NCs conjugated with aptamer targeting ligands can be used for prostate cancer targeting.

Accordingly, NCs can be formulated into solid form when albumin is used as the lyoprotectant. Aptamer-Cy5 NCs can also be made in solid form and then reconstituted to give NCs with similar sizes and targeting capability. At a BSA/Aptamer-Cy5 NC mass ratio of 10, the size of the lyophilized and reconstituted aptamer-Cy5 NC was 212.6 nm (with a polydispersity of 0.386) as compared to NCs with 157.1 nm (with a polydispersity of 0.144) before lyophilization. DLS analysis indicated that the lyophilized and reconstituted aptamer-Cy5 NCs maintain monomodal size distribution. The reconstituted aptamer-Cy5 NCs were then applied in cell-binding studies and analyzed by FACS. Their targeting capability was found to be well preserved during the lyophilization process.

Example 2

Albumin Lyoprotection

As described above in Example 1, albumin can be used as a lyoprotectant to eliminate aggregation of lyophilized nanoparticles, such as various polymer-based nanoparticles, including drug-polymer nanoconjugates. The albumin lyoprotectant methods described herein can be extended to a variety of colloidal systems, in addition to nanoconjugate compositions. For many polymeric sub-micrometer particles, instability during long term storage can limit their otherwise broad clinical applications. To solve instability problems, the particles can be co-formulated with albumin, for example, as described in Example 1. The albumin can be a mammal serum albumin, such as bovine serum albumin or human serum albumin.

Examples of polymer-based particles that can be lyoprotected using albumin to provide non-aggregating solid-form preparations include biodegradable polymers such as polylactide, polyglycolide, and their copolymer poly(lactide-co-glycolide); polycaprolactones; polyacrylates; polyanhydrides; poly(ortho esters); poly (amino esters); polypeptides; and polysaccharides; as well as nonbiodegradable polymers such as polyacrylics, poly(vinyl chloride-co-acetate), polystyrene, and their copolymers. The albumin lyoprotection methods can also be extended to crosslinked polymer networks, such as those used for stents, sutures, or tissue implants, that include one or more of the aforementioned polymers or their copolymers. Colloidal inorganic particulate systems can also be lyoprotected using albumin. Examples of suitable colloidal systems can include carbon nanotubes, graphene, quantum dots, iron oxide, silica particles, metal organic frameworks, gold nanoparticles, silver nanoparticles, platinum nanoparticles, various metal oxide nanoparticles, and their hybrids. The albumin lyoprotection methods can further be extended to organic-inorganic hybrids colloidal systems. Conventional liposome delivery vehicles and the corresponding liposome hybrid with nanoparticles can also be lyoprotected using albumin.

Example 3

In Vitro Aptamer Targeting Capability Validation After Freeze Drying

As described above, it has been demonstrated that NCs can be formulated into solid non-aggregating formulations when albumin is used as a lyoprotectant. Applicants then tested whether aptamer-Cy5 NCs can be made in solid form and then reconstituted to give NCs with similar sizes and targeting capability.

Figure 11:
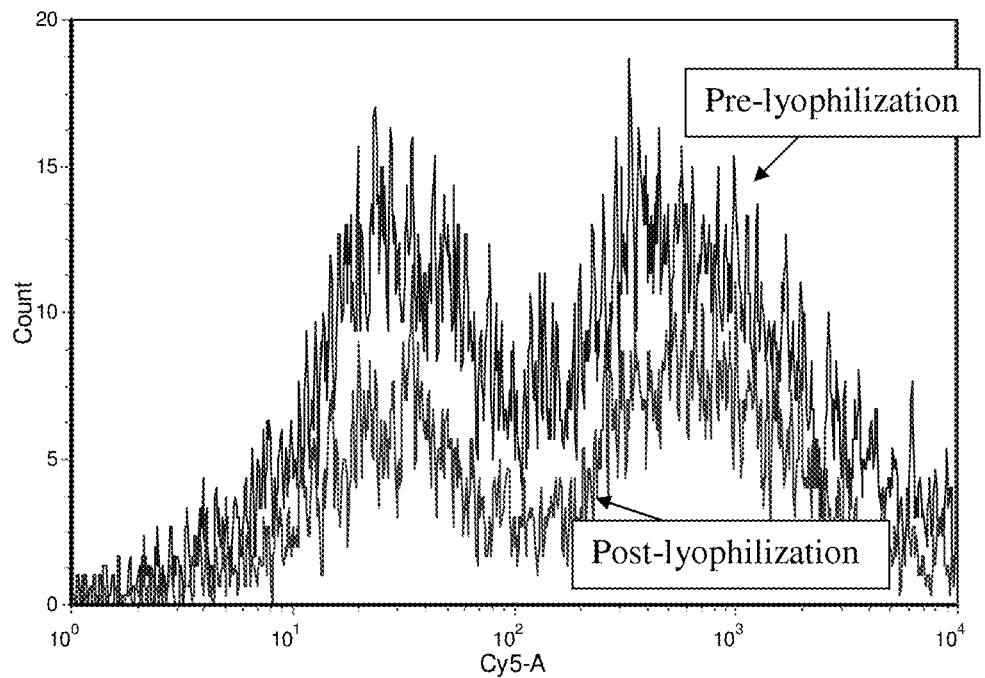
FIG. 11. Fluorescent Activated Cell Sorting (FACS) analysis of aptamer-Cy5 NCs before and after lyophilization; LNCaP cell uptake study within 6 hours.
Figure 12:
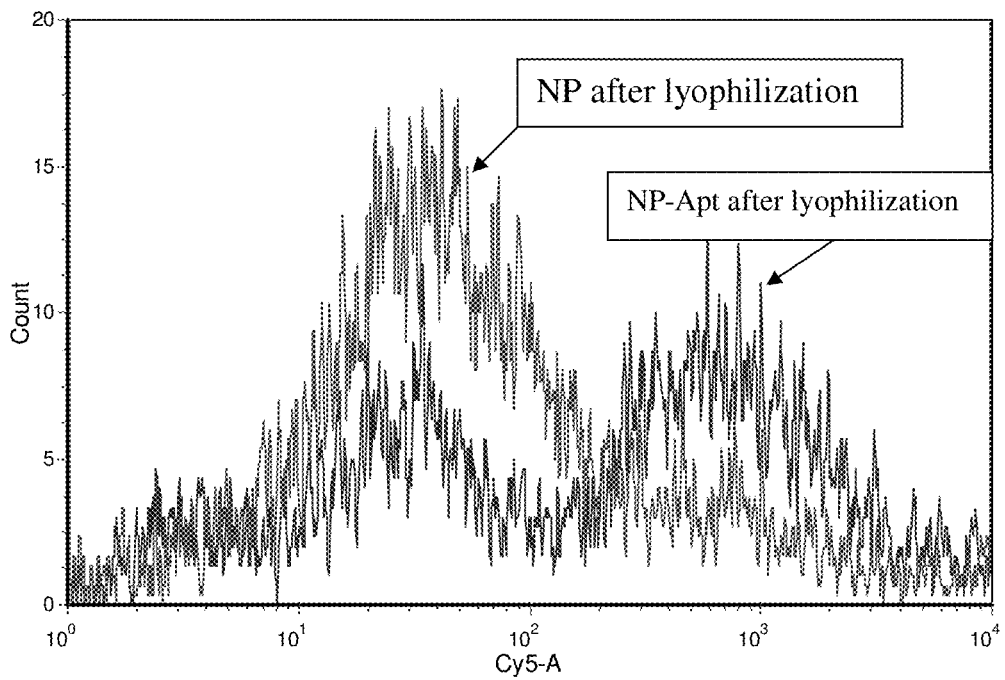
FIG. 12. Fluorescent Activated Cell Sorting (FACS) analysis of aptamer-Cy5 NCs after lyophilization and Cy5 NCs after lyophilization; LNCaP cell uptake study within 6 hours.

At a BSA/Aptamer-Cy5 NC mass ratio of 10:1, the size of the lyophilized and reconstituted aptmaer-Cy5 NC was 212.6 nm (with a DLS polydispersity of 0.386) as compared to NCs with 157.1 nm diameters (with DLS polydispersity of 0.144) before lyophilization. DLS analysis indicated that the lyophilized and reconstituted aptamer-Cy5 NCs maintain monomodal size distribution. The reconstituted aptamer-Cy5 NCs were then applied in cell-binding studies and analyzed by FACS; their targeting capability was found to be well preserved during the lyophilization process (FIG. 11), compared to the particles without aptamer after freeze drying (FIG. 12). These results demonstrate that the NCs formulated as described herein can be clinically translated and are suitable for treating cancer in humans.

Example 4

Tumor Prevention/Inhibition Study Using PLA-Ptxl NCs

To access the ability of paclitaxel-loaded nanoparticles to inhibit establishment of lung cancer in an in vivo model mimicking microscopic disease that can remain when the surgical margin is close to the tumor, Ptxl-PLA NCs were evaluated in a rapidly growing subcutaneous tumor model. Specifically, the ability of Ptxl-PLA NCs to prevent establishment of rapidly growing LLC tumors in C57Bl/6 female mice compared to Ptxl alone (in a clinical formulation) and controls without any drugs was assessed. In these experiments, 1,000,000 LLC tumor cells plus Ptxl-LA$_{25}$/PLGA-mPEG nanoparticles containing a total dose of 5 or 50 mg/kg incorporated Ptxl were injected subcutaneously into the flank of a mouse. Other groups received the injection of 1,000,000 LLC cells alone or LLC cells mixed with Ptxl solubilized with 1:1 Cremophor EL/ethanol as used clinically at 5 mg/kg dosage.

Figure 13:
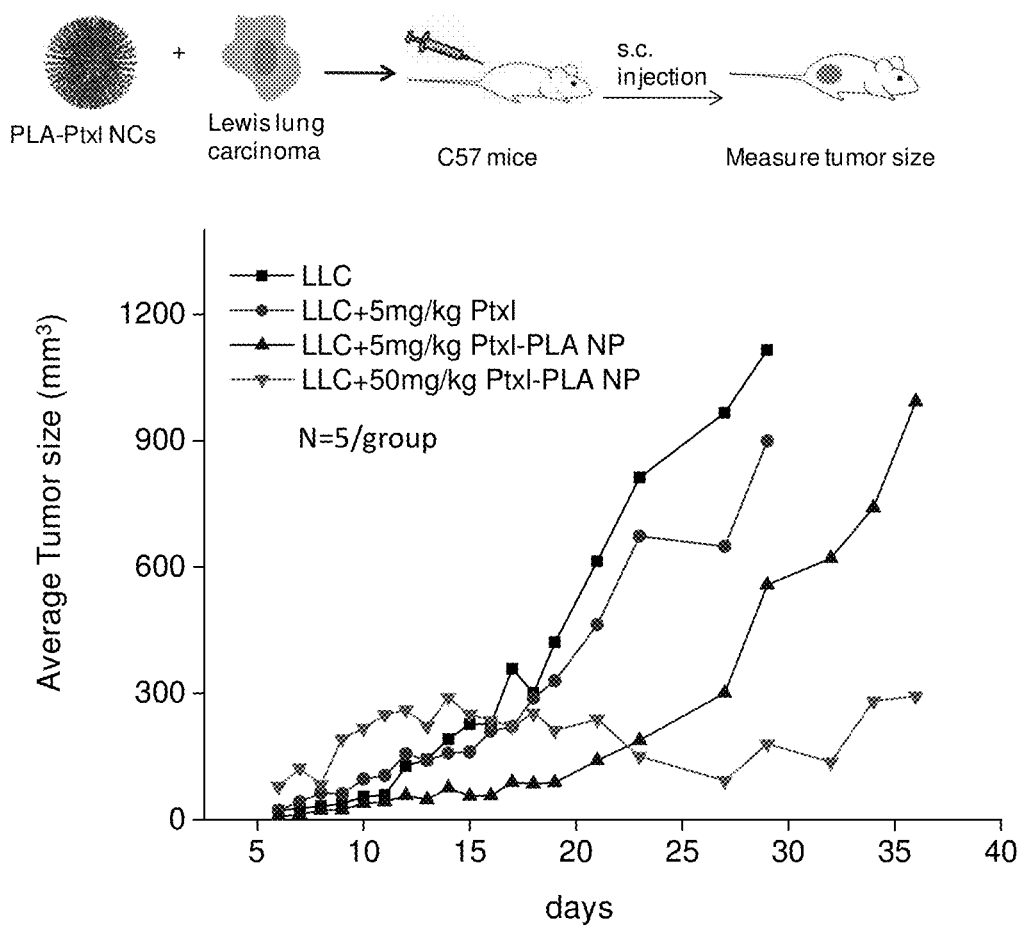
FIG. 13. A tumor prevention/inhibition study of PLA-Ptxl NCs.

At 25 days, large tumors were noted at the site where LLC cells were co-injected with media alone, or paclitaxel alone. In contrast, sites receiving LLC cells plus paclitaxel-loaded nanoparticles showed a significantly reduced incidence of tumor and tumor burden. After 30 days, growing tumors were noticed at the site where LLC cells were co-injected with Ptxl-LA$_{25}$ NCs at 5 mg/kg; whereas tumors sizes were maintained for the group co-injected with Ptxl-LA$_{25}$ NCs at 50 mg/kg (FIG. 13), thus demonstrating the inhibitory capability of the NCs. The observation that animals receiving all other treatment regimes besides the Ptxl loaded NCs (50 mg/kg) rapidly developed large tumors indicates that NCs are an effective delivery vehicle for Ptxl and other drugs described herein.

Example 5

In Vivo Evaluation of PLA-Doxo NC Toxicity

Figure 14:
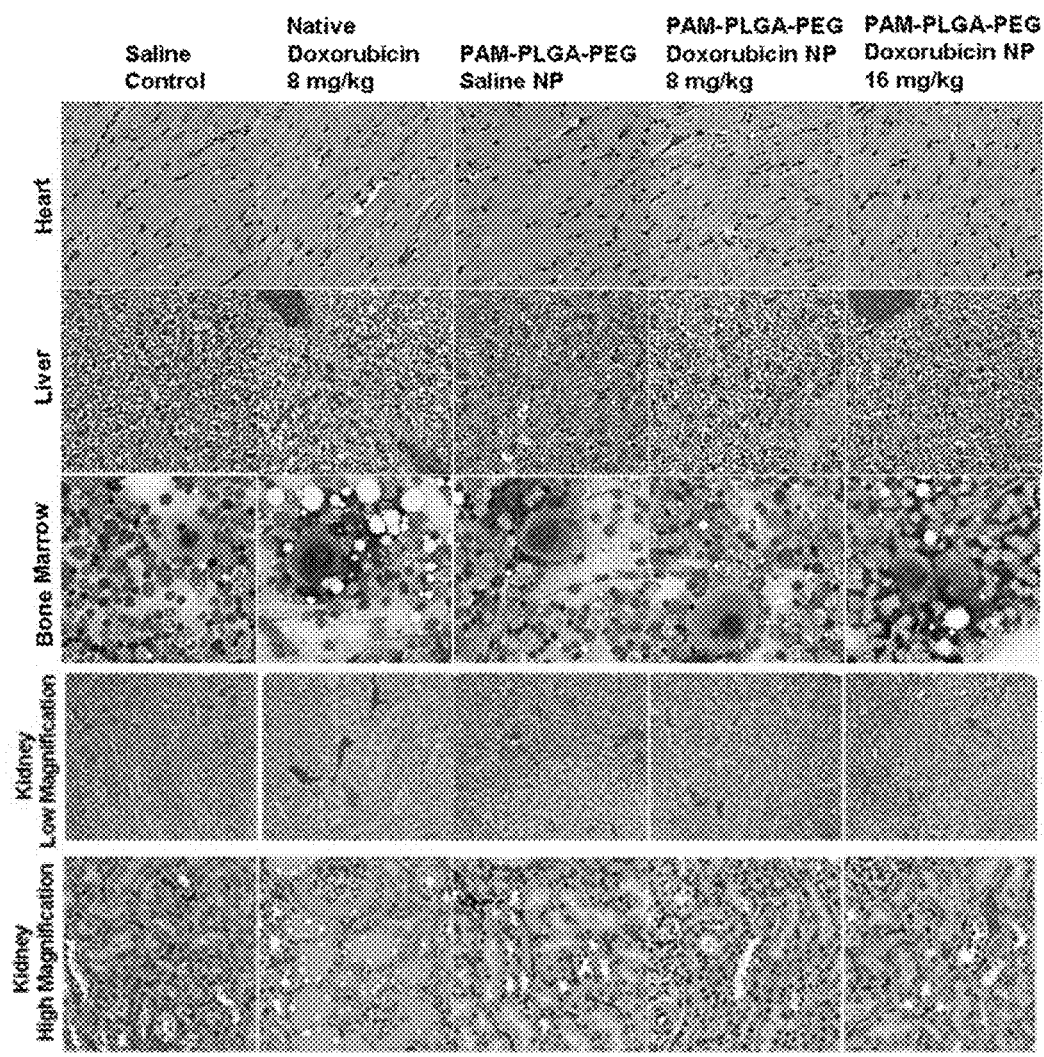
FIG. 14. In vivo toxicity analysis of PLA-Doxo NCs (with pamidronate ligand); histological analysis of balb/c mice tissue sections.

A histological analysis of balb/c mice tissue sections was carried out (FIG. 14). Mice were dosed (i.v.) with doxorubicin ("Doxo") (8 mg/kg), PLA-PEG-PAM / Doxo-LA$_{25}$ (8 and 16 mg/kg), saline, and blank NPs. Tissue sections from the mice kidney indicated that doxorubicin (8 mg/kg) has severe toxicity to kidneys, while NCs with a 16 mg/kg doxorubicin equivalent did not show any toxicity to kidney tissues. These results demonstrate that the NCs formulated as described herein can be clinically translated and are less toxic than drugs administered in non-conjugated form.

Example 6

In Vivo Tumor Targeting Study Of Aptamer-PLA-NCs

Pamidronate (PAM), a well-know bisphosphonate drug, was selected as a targeting ligand for bone-tumor cancer chemotherapy. PAM was conjugated to PLA-PEG-COOH through a conjugation reaction using EDC/NHS. The resulting PLA-PEG-PAM was purified by dialysis. Doxo-LA$_{25}$ was mixed with PLGA-mPEG/PLA-PEG-PAM in DMF and nanoprecipitation to prepare NPs averaging 126 nm in diameter.

To validate the potential of Doxo-LA$_{25}$/PLA-PEG-PAM NPs for bone tumor therapy, the toxicity of NPs to tissues in a histological study in balb/c mice was evaluated. After staining by hematoxylin and eosin, kidney tissue damage was found in the group treated with 8 mg/kg Doxo; while no kidney tissue toxicity are found in groups received NPs with same and twice Doxo equivalent dose (8 and 16 mg/kg) and controls. In addition, PLA-PEG-PAM NPs itself did not exhibit in vivo toxicity in histological tissue analysis (FIG. 14). The study demonstrated that Doxo-LA$_{25}$/PLA-PEG-PAM can be further applied to preclinical studies for bone cancer therapy. The in vivo tissue toxicity was also confirmed by infusion PLA-PEG-PAM NPs (50 mL saline solution, 3 mg/mL NPs) to dogs (n=5), and no severe or abnormal symptoms were observed even days after injection.

It is noted that PAM can be labeled with $^{99m}$Tc for real time in vivo imaging, facilitating the monitoring of the targeting process. The potential to employ the radionuclide technetium-99m with its optimal decay characteristics into targeting molecules has been the foremost consideration in developing diagnostic radiopharmaceuticals. $^{99m}$Tc-labeled radio-pharmaceuticals are preferred over other isotopes because of the ideal nuclear properties of the isotope, as well as its widespread availability from commercial generator columns. $^{99m}$Tc emits a 140 keV γ-ray with 89% abundance, which is ideal for imaging with commercial γ cameras.

Figure 15:
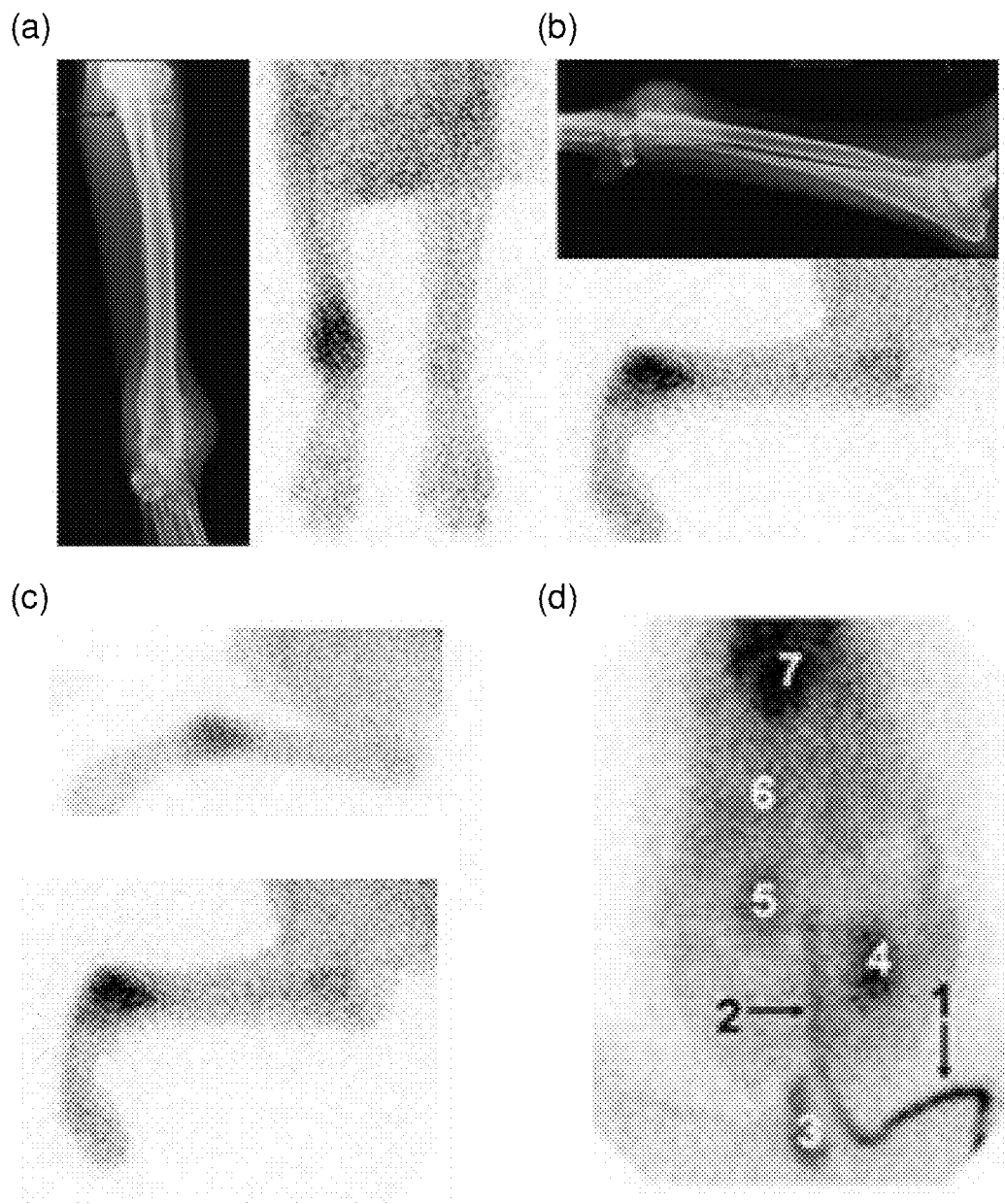
FIG. 15. In vivo targeting of PLA-PEG NCs with PAM.

PLA-PEG-PAM NPs were in situ labeled with sodium $^{99m}$TcO$_4$ in saline and the reductant SnCl$_2$ and were quickly used in an in vivo bone tumor targeting study in dog. Bone tumors were grown in one leg of the dog and confirmed by X-ray analysis. The accumulation of PLA-PEG-PAM NPs with $^{99m}$Tc labeling was observed in γ camera images, and the amount increased over time even in only 2 hours after injection (FIG. 15). Whole body biodistribution analysis of the dog showed NPs were not accumulated in liver and kidney 2 hours after infusion, indicating that the NPs with PAM can quickly target bone tumors in vivo. It was noted that the intensity also increased in the bladder site after 30 hours, suggesting that the $^{99m}$Tc reagents might be sheared off from NPs after prolonged periods of time.

FIG. 15 illustrates the in vivo imaging of PLA-PEG-PAM NPs labeled with $^{99m}$Tc for bone tumor in dog: X ray and $^{99m}$Tc radioactive γ imaging of (a) front and (b) lateral view of a dog leg with one side implanted with a tumor. The intensity (black) area of $^{99m}$Tc radioactive images indicated the accumulation of the NPs. (c) Kinetic study of NPs accumulation in bone tumor of 1 hour (up) and 2 hours (bottom) after injection. (d) Whole body biodistribution of NPs in dog 5 minutes after injection (top view). Site number: 1: lateral saphenous vein (NPs infusion site); 2: caudal vena cava; 3: urinary bladder; 4: left kidney; 5: right kidney; 6: liver; 7: heart.

Figure 16:
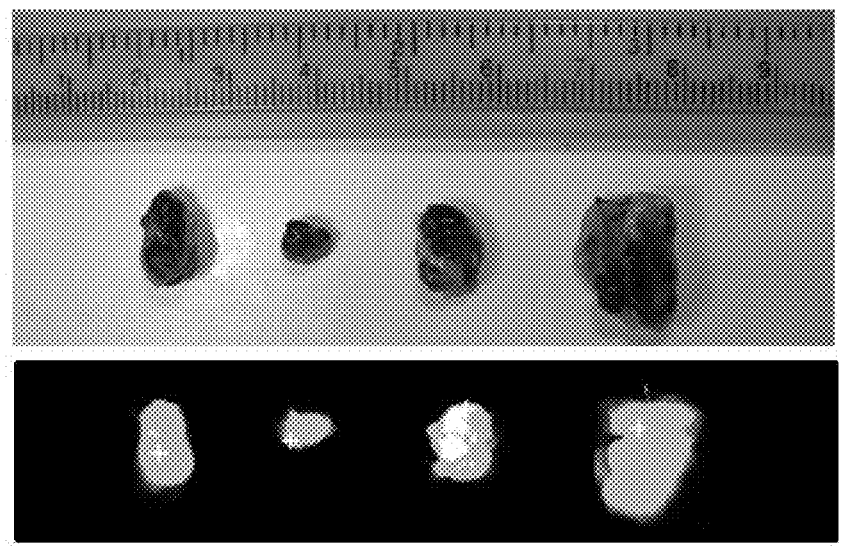
FIG. 16. In vivo tumor targeting of aptamer-NCs.

FIG. 16 illustrates further in vivo tumor targeting of aptamer-NCs. The tumor model was the implantation of a canine malignant endothelial tumor line, SB-HSA (for PSMA aptamer targeting), a model of tumor neovasculature. Five million cells were injected into the flank of NOD-SCID mice and the mice were allowed to grow for approximately 4 months. After the tumors grew to approximately 10 mm×10 mm, the mice were treated with i.v. injections of PLA-PEG-NIR/PLA-PEG-aptamer (NIR: near infrared cyanine dye). Four mice received this treatment and showed clear evidence of tumor accumulation of the aptamer particles (FIG. 16). Preliminary biodistribution analysis showed a % ID/g (ID: injection dose) for tumor of 7.83% (higher than a previous LNCaP prostate cancer model); spleen and liver were 40.10 and 18.28, respectively. These results demonstrate that the NCs formulated as described herein can be clinically translated and have significant improved properties over known treatments.

Example 7

Pharmaceutical Dosage Forms

The following formulations illustrate representative pharmaceutical dosage forms that may be used for the therapeutic or prophylactic administration of a composition described herein, (hereinafter referred to as 'Composition X'):

| (i) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (ii) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (iii) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (iii) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

One of ordinary skill in the art will appreciate that starting materials, e.g., cyclic monomers, drugs and other chemical species having at least one hydroxyl group, biological materials, reagents, e.g., ring-opening polymerization catalysts, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A drug-polymer nanoconjugate composition comprising drug-polymer nanoconjugate particles having a block copolymer coating, and an albumin coating;
   wherein the drug-polymer nanoconjugate particles comprise one or more drugs and one or more polymers, and the one or more drugs of the drug-polymer nanoconjugate particles are individually covalently bonded to initiation points of individual polymers of the drug-polymer nanoconjugate particles through ether or thioether moieties;
   the one or more polymers of the drug-polymer nanoconjugate particles comprise polyester, polycarbonate, polyphosphate, polysiloxane, polyphosphazane, polypeptide, or amino acid oligomers segments, or a combination thereof;
   the block copolymer coating comprises PEG and lactide blocks; and
   the block copolymer coating is coated with an amount of albumin effective to at least substantially prevent aggregation of the drug-polymer nanoconjugate particles when in contact with other drug-polymer nanoconjugates particles, wherein the ratio of the mass of albumin coating to the total mass of the drug-polymer nanoconjugate particles is about 2:1 to about 20:1; and
   wherein the composition has a diameter of about 2 nm to about 300 nm and a mass of less than 2 wt. % of total drugs that are not covalently bonded to the polymer.

2. The composition of claim 1 further comprising one or more cell-targeting agents covalently bonded to the surface of the drug-polymer nanoconjugate particles or to the block copolymer coating.

3. The composition of claim 1 wherein the diameter of the combined drug-polymer nanoconjugate particles, block copolymer coating, and albumin coating, is less than about 200 nm.

4. The composition of claim 1 wherein the mass of the composition comprises less than 0.5 wt. % of total drugs that are not covalently bonded to a polymer.

5. The composition of claim 1 wherein the block copolymer coating comprises one or more PLA-PEG diblock copolymers, one or more PLA-PEG-PLA triblock copolymers, or a combination thereof.

6. The composition of claim 1 wherein the molecular weight of the PEG block of the block copolymer coating is about 400 to about 40,000, and the molecular weight of the lactide block of the block copolymer coating is about 1,000 to about 250,000.

7. The composition of claim 1 wherein the molecular weight of the PEG block of the block copolymer coating is about 5,000, and the molecular weight of the lactide block of the block copolymer coating is about 5,000 to about 50,000.

8. The composition of claim 1 wherein the drug-polymer nanoconjugate particles remain non-aggregated in the presence of other drug-polymer nanoconjugate particles for more than 24 hours when contacted with the other drug-polymer nanoconjugate particles in water or in an aqueous solution.

9. The composition of claim 2 wherein the cell-targeting agent covalently bonded to the surface of the drug-polymer nanoconjugate particles comprises an aptamer.

10. The composition of claim 1 wherein the mass ratio of the drug-polymer nanoconjugate particles to the block copolymer coating is about 0.1 to about 10.

11. The composition of claim 1 wherein the albumin is a mammalian serum albumin.

12. A composition comprising a plurality of nanoconjugate compositions of claim 1 wherein the nanoconjugate particle size distribution is monomodal.

13. The composition of claim 12 wherein the molecular weight distribution of the drug-polymer nanoconjugate particles is less than 1.05.

14. The composition of claim 12 wherein the nanoconjugate particles remain non-aggregated when exposed to a PBS solution for more than 30 minutes.

15. A method for delivering the drug of drug-polymer nanoconjugate particles to the surface or interior of a cell comprising contacting a cell with a composition of claim 1, so that the drug-polymer nanoconjugate particles associate with the cell for a period of time sufficient for the drug-polymer nanoconjugate particles to release the drug from the polymer, thereby delivering the drug to the surface or interior of the cell.

16. The method of claim 15 wherein the cell is a prostate cancer cell, breast cancer cell, lung cancer cell, pancreatic cancer cell, or colon cancer cell.

17. The composition of claim 1 wherein one or more of the drugs of the drug-polymer nanoconjugate is doxorubicin, pamidronate, daunorubicin, epirubicin, mitoxantrone, bleomycin $A_2$, bleomycin $B_2$, vincristine, vinblastine, vinorelbine, vindesine, podophyllotoxin, etoposide, teniposide, paclitaxel, docetaxel, irinotecan, topotecan, abacavir, acyclovir, didanosine, darunavir (TMC-114), ribavirin, natamycin, fluconazole, posaconaczole, voriconazole, caspofungin, amphotericin B, phenoxyethanol, tipranavir (TPV), saquinavir (SQV), ritonavir (RTV), indinavir, nelfinavir (NFV), amprenavir (APV), lopinavir (ABT-378), atazanavir (ATV), vinorelbine bitartrate, fulvestrant, sarcodictyins, camptothecin, bryostatin 1, (+)-cylindricine, (+)-lactacystin, aeruginosin 298-A, (+)-fostriecin, garsubellin A/hyperforin, (S)-oxybutynin, epothilone A, zidovudine (AZT), lamivudine (3TC), emtricitabine (FTC), bamethane, ethamivan, hexachlorophene, salicylanilide, pyrocatechin, thymol, pentazocine, phloroglucinol, eugenol, niclosamide, terbutaline, dopamine, methyldopa, norepinephrine, alpha-naphthol, adrenaline, phenylephrine, metaraminol, fenoterol, bithionol, alpha-tocopherol, isoprenaline, salbutamol, chlorogenic acid or an alkyl ester thereof, captopril, amoxicillin, betaxolol, masoprocol, genistein, daidzein, daidzin, acetylglycitin, equol, glycitein, iodoresiniferatoxin, SB202190, tyrphostin SU1498, or a combination thereof.

18. A method of reducing or eliminating nanoparticle aggregation comprising:
    contacting a plurality of nanoparticles with a block copolymer that comprises poly(ethylene glycol) and poly(lactide) blocks to provide block copolymer coated particles; and
    coating the block copolymer coated particles with albumin, thereby reducing or eliminating nanoparticle aggregation of the nanoparticles
    wherein the nanoparticles comprise the drug-polymer nanoconjugate composition of claim 1.

* * * * *